United States Patent
Zhu et al.

(10) Patent No.: US 8,951,702 B2
(45) Date of Patent: Feb. 10, 2015

(54) CHARGE TRANSPORT MATERIAL THAT IS AN ETHYLENE COMPOUND, ELECTROPHOTOGRAPHIC PHOTORECEPTOR CONTAINING THE CHARGE TRANSPORT MATERIAL, AND PROCESS FOR PRODUCING THE ELECTROPHOTOGRAPHIC PHOTORECEPTOR

(75) Inventors: Fengqiang Zhu, Matsumoto (JP); Yoichi Nakamura, Matsumoto (JP); Ikuo Takaki, GuangDong (CN); Seizo Kitagawa, Matsumoto (JP); Shinjirou Suzuki, Matsumoto (JP)

(73) Assignee: Fuji Electric Co., Ltd., Kawasaki-Shi (JP)

( * ) Notice: Subject to any disclaimer, the term of this patent is extended or adjusted under 35 U.S.C. 154(b) by 33 days.

(21) Appl. No.: 12/921,374

(22) PCT Filed: Jul. 9, 2009

(86) PCT No.: PCT/JP2009/062505
§ 371 (c)(1),
(2), (4) Date: Mar. 21, 2011

(87) PCT Pub. No.: WO2010/007930
PCT Pub. Date: Jan. 21, 2010

(65) Prior Publication Data
US 2011/0183246 A1    Jul. 28, 2011

(30) Foreign Application Priority Data

Jul. 18, 2008   (JP) ................. 2008-187022

(51) Int. Cl.
| G03G 5/047 | (2006.01) |
| C07C 211/54 | (2006.01) |
| G03G 5/06 | (2006.01) |

(52) U.S. Cl.
CPC ............ *C07C 211/54* (2013.01); *G03G 5/0614* (2013.01); *G03G 5/0668* (2013.01); *G03G 5/0696* (2013.01)
USPC .................. 430/58.85; 430/58.05; 430/58.65; 430/59.1; 430/59.4; 430/59.5; 430/127; 430/133

(58) Field of Classification Search
USPC .............. 430/58.05, 58.65, 58.85, 59.1, 59.4, 430/59.5, 127, 133
See application file for complete search history.

(56) References Cited

U.S. PATENT DOCUMENTS

| 2,297,691 | A | 10/1942 | Carlson |
| 3,816,118 | A | 6/1974 | Byrne |
| 3,825,422 | A | 7/1974 | Gruber et al. |
| 5,018,105 | A | 5/1991 | Miyanishi |
| 5,952,139 | A | 9/1999 | Takeuchi et al. |

FOREIGN PATENT DOCUMENTS

| CA | 1119449 | A | | 3/1996 | |
| JP | 53-89433 | | | 8/1978 | |
| JP | 57-148745 | A | | 9/1982 | |
| JP | 60-104951 | A | | 6/1985 | |
| JP | 63-292137 | | * | 11/1988 | ............... G03G 5/06 |
| JP | 63-292141 | | * | 11/1988 | ............... G03G 5/06 |
| JP | 01-245263 | A | | 9/1989 | |
| JP | 01-250961 | A | | 10/1989 | |
| JP | 02-264263 | A | | 10/1990 | |
| JP | 05-112508 | A | | 5/1993 | |
| JP | 07-120950 | A | | 5/1995 | |
| JP | 8-33660 | | | 3/1996 | |
| JP | 10-063020 | A | | 3/1998 | |
| JP | 10-104859 | | * | 4/1998 | ............... G03G 5/06 |
| JP | 10-104859 | A | | 4/1998 | |
| JP | 10-228121 | A | | 8/1998 | |
| JP | 11-184108 | A | | 7/1999 | |
| JP | 2000-081757 | | * | 3/2000 | |
| JP | 2000-081757 | A | | 3/2000 | |
| JP | 2003-021925 | A | | 1/2003 | |
| JP | 2003-81969 | | * | 3/2003 | ........... C07D 333/08 |

OTHER PUBLICATIONS

Translation of JP 2000-081757 published Mar. 2000.*
Translation of the abstract of JP 63-292141 published Nov. 1988.*
Translation of abstract of JP 63-292137 published Nov. 1988.*
Translation of JP 2003-81969 published Mar. 2003.*
Translation of JP 10-104859 published Apr. 1998.*
Japanese Office Action dated Dec. 18, 2012 with English translation.

* cited by examiner

*Primary Examiner* — Peter Vajda
(74) *Attorney, Agent, or Firm* — Rabin & Berdo, P.C.

(57) ABSTRACT

A charge transport material having reduced photodeterioration is disclosed to be an ethylene compound having an ethylene double bond site, having a structure in which four different substituents are substituted at the ethylene double bond site, and having general formula (I) below

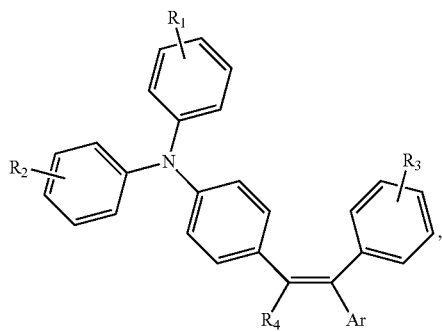

(I)

where $R_1$, $R_2$ and $R_3$ are each independently a hydrogen atom, a halogen atom, an alkyl group of 1 to 6 carbons or an alkoxyl group of 1 to 6 carbons; $R_4$ is phenyl or tolyl; and Ar is one group selected from the group consisting of naphthyl, biphenyl, anthryl, xylyl, and phenanthryl. An electrophotographic photoreceptor and process for producing the electrophotographic photoreceptor also are disclosed. The electrophotographic photoreceptor includes a conductive substrate; and a photosensitive layer provided on the conductive substrate that includes the charge transport material.

14 Claims, 2 Drawing Sheets

CHARGE TRANSPORT MATERIAL THAT IS AN ETHYLENE COMPOUND, ELECTROPHOTOGRAPHIC PHOTORECEPTOR CONTAINING THE CHARGE TRANSPORT MATERIAL, AND PROCESS FOR PRODUCING THE ELECTROPHOTOGRAPHIC PHOTORECEPTOR

BACKGROUND OF THE INVENTION

1. Field of the Invention

The present invention relates to an electrophotographic photoreceptor (also referred to as simply a "photoreceptor" below) and a process for producing such an electrophotographic photoreceptor. More specifically, the invention relates to an electrophotographic photoreceptor which is made primarily of a conductive substrate and a photosensitive layer containing an organic material, and which is used in, for example, electrophotographic printers, copiers and facsimile machines, and relates also to a process for producing such an electrophotographic photoreceptor.

2. Background of the Related Art

Image-forming methods that employ electrophotographic technology are used widely not only in office copiers, printers and plotters, and in digital multifunctional devices which combine the functions of these pieces of equipment, but also more recently in small printers and facsimile machines for personal use. Ever since Carlson's invention (U.S. Pat. No. 2,297,691 (Patent Document 1) of a photoreceptor for an electrophotographic device, many photoreceptors have been developed, and photoreceptors which use organic materials have become particularly commonplace.

Such photoreceptors include multi layer photoreceptors composed of a conductive substrate such as aluminum having stacked thereon: an undercoat layer such as an anodic oxide film or a resin film; a charge generation layer containing an organic pigment having photoconductivity, such as a phthalocyanine or azo pigment; a charge transport layer containing molecules having a partial structure which participates in charge hopping conduction, such as an amine or hydrazine coupled to a π-electron conjugated system; and a protective layer. Single layer type photoreceptors which combine the charge generation and charge transport functions are also known. A single layer type photoreceptor may also have an undercoat layer.

Each of these layers is generally formed by a method that involves dip-coating the conductive substrate in a coating obtained by dissolving or dispersing a pigment having charge-generating, light-scattering and other functions or a charge transport material which assumes the role of transporting charges in a suitable resin solvent. Such a method is used because it has an excellent mass productivity.

Recent electrophotographic devices employ predominantly the so-called reversal development process which uses a semiconductor laser having an emission wavelength of about 450 to 780 nm or light-emitting diodes as the exposure light source to convert digital signals for images, text and the like into light signals, shines the light signals onto an electrically charged photoreceptor so as to form an electrostatic latent image on the surface of the photoreceptor, and renders the latent image visible by means of a toner.

Moreover, in such electrophotographic devices, phthalocyanines, which have a large light absorbance in the semiconductor laser emission wavelength region compared with other charge generation materials and also have an excellent charge generating ability, are being widely studied as photosensitive layer materials. In particular, photoreceptors which use various types of phthalocyanines having aluminum, indium, vanadium, titanium, etc. as the center metal are known today (Japanese Patent Application Laid-open No. S53-89433 (Patent Document 2), U.S. Pat. No. 3,816,118 (Patent Document 3), Japanese Patent Application Laid-open No. S57-148745 (Patent Document 4), and U.S. Pat. No. 3,825,422 (Patent Document 5).

Methods for electrically charging photoreceptors include a non-contact charging system in which a charging member that operates such as by corona discharge from a scorotron remains in a non-contact state with the photoreceptor, and a contact charging system in which a charging member in the form of a roller composed of conductive rubber or a brush composed of conductive fibers comes into contact with the photoreceptor. Compared with a non-contact charging system, such a contact charging system has a short discharge distance in open air. As a result, it generates little ozone, the power supply voltage may be low, and the system is maintenance-free because there is no deposition on the charging member of scum that arises due to discharge. Moreover, such a contact charging system is able to keep the charge potential on the photoreceptor uniform. Accordingly, medium and small-size electrophotographic devices predominantly use contact charging systems because such a system makes it possible to achieve devices which are more compact, lower cost, and less environmentally polluting.

However, it is known from experimental results on many compounds that, when a charge generation layer and a charge transport layer are combined to form a photosensitive layer, very few compounds satisfy the photoreceptor characteristics and conditions required for practical use. In particular, few compounds satisfy the repeated charging and exposure characteristics of known electrophotographic processes; when repeated charging and exposure is carried out, this invites a rise in residual potential that is believed to be caused by charge trapping and accumulation in the charge transport layer. Owing to this influence, changes in image density due to repetition arise in the reversal development process employed in printers and the like. Such changes are presumed to be due to light-induced fatigue. This problem similarly arises also in single layer type photoreceptors obtained by dispersing the above phthalocyanine pigment, a bisazo pigment or the like in a resin binder, and applying the resulting dispersion.

The addition of specific additives to a charge transport layer in order to prevent photodeterioration is known. For example, Japanese Patent Application Laid-open No. H10-228121 (Patent Document 6) discloses art for adding an orange dye compound, Japanese Examined Patent Publication No. H8-33660 (Patent Document 7) discloses art for adding an orange colorant, and Japanese Patent Application Laid-open No. H11-184108 (Patent Document 8) discloses art for adding a compound having a maximum absorption wavelength at 480 nm.

Also, to prevent a decline in electrostatic properties due to exposure-induced fatigue, Japanese Patent Application Laid-open No. S60-104951 (Patent Document 9), Japanese Patent Application Laid-open No. H2-264263 (Patent Document 10), Japanese Patent Application Laid-open No. H5-112508 (Patent Document 11), and Japanese Patent Application Laid-open No. H7-120950 (Patent Document 12) disclose, as charge transport materials, ethylene compounds having many double bonds.

However, as mentioned in Patent Documents 6 to 8 and elsewhere, the art for adding specific additives to a charge transport layer is limited to phthalocyanine pigments or specific charge transport materials. These documents describe nothing other than photodeterioration-preventing effects for preventing photodegradation of the charge transport material, etc. by taking into account light absorption. The compounds mentioned in Patent Documents 9 to 12 did not exhibit sufficient effects for light-induced fatigue.

It is therefore an object of the present invention to provide an ethylene compound and a charge transport material which have a low photodeterioration. Further objects of the invention are to provide an electrophotographic photoreceptor which has a low light-induced fatigue and is capable of preventing the rise in residual potential that accompanies fatigue; an electrophotographic photoreceptor which, owing to these characteristics, has stable properties as an electrophotographic photoreceptor even when used for an extended period of time, and can stably obtain satisfactory images; and a process for producing such an electrophotographic photoreceptor.

SUMMARY OF THE INVENTION

The inventors have conducted extensive investigations and repeated experiments on electrophotographic photoreceptors which can prevent photodeterioration and light-induced fatigue of the photoreceptor in repeated use, and can also prevent accompanying increases in the residual potential. As a result, they have discovered that when compounds having specific tetrasubstituted ethylene structures are used, because the compounds do not readily undergo photodegradation, photodeterioration can be suppressed and, moreover, because the compounds have a structure which does not readily undergo Z/E (cis-trans) isomerization, light-induced fatigue is suppressed. The inventors have also found that because photodeterioration and light-induced fatigue can be prevented, electrophotographic photoreceptors endowed with truly outstanding properties can be provided. These discoveries ultimately led to the present invention.

That is, the present invention relates to an ethylene compound of general formula (I)

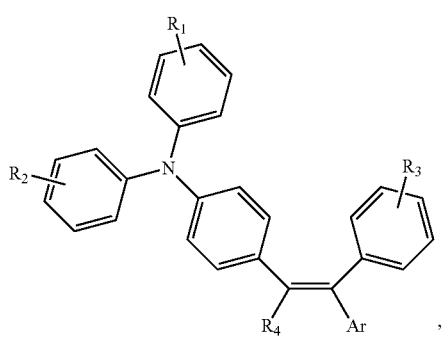

and to a charge transport material containing the same. The electrophotographic photoreceptor of the invention is an electrophotographic photoreceptor having a conductive substrate and at least a photosensitive layer on the conductive substrate, and the photosensitive layer contains an ethylene compound of general formula (I) below

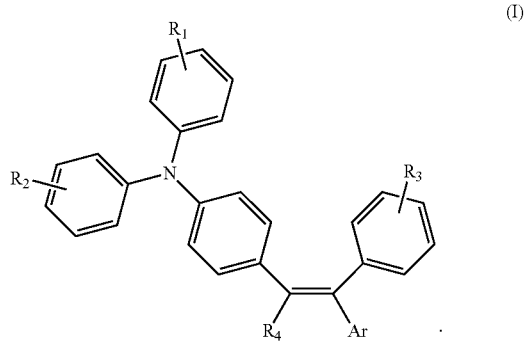

In above general formula (I), $R_1$, $R_2$ and $R_3$ are each independently a hydrogen atom, a halogen atom, an alkyl group of 1 to 6 carbons or an alkoxyl group of 1 to 6 carbons which may be substituted; $R_4$ is an alkyl group of 1 to 3 carbons, phenyl or tolyl; and Ar is an aryl group of 7 to 20 carbons or a heterocyclic group. The compound of formula (I) may have a structure in which the positions of $R_4$ and Ar assume either a Z-form (cis form) or an E-form (trans form) alone, or may be a mixture of both forms. In addition, compounds of formula (I) having other structures may also be included.

The present invention may be an electrophotographic photoreceptor wherein the photosensitive layer includes at least a charge generation material, a charge transport material and a resin binder, and includes the ethylene compound of general formula (I) as the charge transport material.

The present invention may be, for example, a multi layer electrophotographic photoreceptor having a conductive substrate, a charge generation layer containing at least a charge generation material formed on the conductive substrate, and a charge transport layer containing at least a charge transport material formed on the charge generation layer. Alternatively, the present invention may be a multi layer electrophotographic photoreceptor having a conductive substrate, a charge transport layer containing at least a charge transport material formed on the conductive substrate, and including thereon at least a charge transport material and a charge generation material. Or the present invention may be a single layer type electrophotographic photoreceptor composed of a single photosensitive layer.

Charge generation materials that may be used in the present invention include titanyl phthalocyanine or metal-free phthalocyanine, or both may be included.

The inventive process for producing an electrophotographic photoreceptor involves forming a photosensitive layer by applying a liquid coating containing an ethylene compound of general formula (I) below

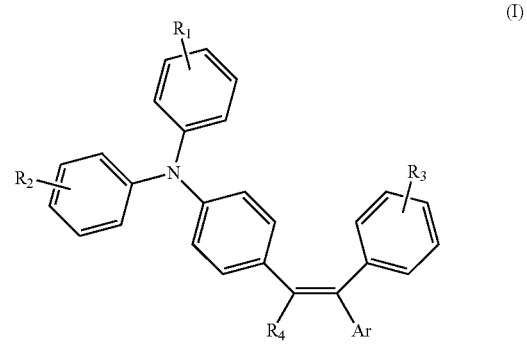

onto a conductive substrate. In general formula (I), $R_1$ to $R_4$ and Ar have the same meanings as indicated above.

In the inventive electrophotographic photoreceptor having a conductive substrate and at least a photosensitive layer on the conductive substrate, the photosensitive layer includes an ethylene compound of above general formula (I), that is, a compound (I) having a structure in which four different substituents have been substituted at the site of a double bond. Because this compound is not readily subject to photodegradation or photodeterioration owing to the steric effects of the substituents, light-induced fatigue can be suppressed. In addition, compared with disubstituted or trisubstituted ethylene compounds, this compound (I), even when irradiated with light for an extended period of time, does not readily give rise to Z/E photoisomerization by a Hula-twist mechanism within the space in a film state, and thus undergoes less photodeterioration. As a result, light-induced fatigue of the photosensitive layer is minimal, thus making it possible to provide an electrophotographic photoreceptor capable of preventing a rise in the residual potential, that is, an electrophotographic photoreceptor which, even when used for an extended period of time, has electrophotographic photoreceptor characteristics which are stable and enables satisfactory images to be stably obtained, and also making it possible to provide a process for producing such an electrophotographic photoreceptor. The Z/E photoisomerization of ethylene compounds via the Hula-twist mechanism is described in, for example, *J. Photochem. Photobiol. A: Chemistry* 2006, 184, 44-49.

For example, it is thought that the ethylene compound with a trisubstituted structure serving as Compound No. 2-4 of Patent Document 9, due to E/Z isomerization by the Hula-twist mechanism which arises even in the relatively limited space within a film, influences the photoreceptor properties due to steric structural changes that arise in the charge transport material within the film. Also, in the case of tetrasubstituted ethylene compounds such as No. 2-53 and No. 2-58, because these have sterically large tetrasubstituents, synthesis by the synthesis method in the final step of the same document is extremely difficult, making large-volume industrial synthesis in a high yield problematic. By contrast, the tetrasubstituted ethylene compound of general formula (I) in the present invention is able to prevent photoisomerization by the Hula-twist mechanism even in the space within a film. In addition, because this tetrasubstituted ethylene compound has a tetrasubstituted structure which is a sterically crowded structure, the ethylene sites are not readily subject to photodegradation by external causes such as ozone or $NO_x$. Moreover, the present invention uses a method which differs from that of Patent Document 9, making industrial production possible.

DETAILED DESCRIPTION OF THE INVENTION

Figure 1:
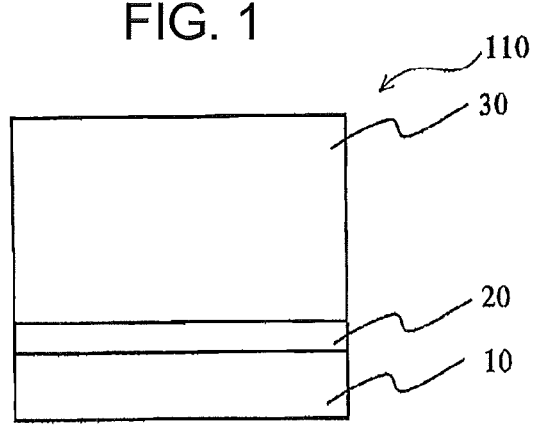
FIG. 1 is schematic cross-sectional diagram showing an example of a single layer type photoreceptor.

Embodiments of the invention are described in detail below.

The ethylene compound of the invention is a compound of general formula (I) below

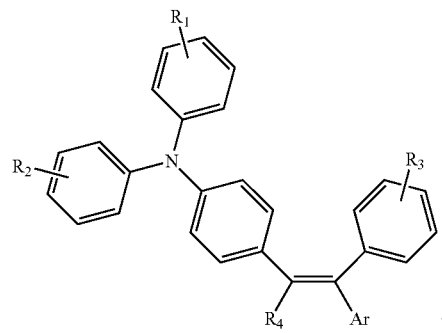

The compound of general formula (I) is also referred to below as Compound (I). Other compounds are similarly denoted.

In above general formula (I), $R_1$, $R_2$ and $R_3$ are each independently a hydrogen atom, a halogen atom, an alkyl group of 1 to 6 carbons or an alkoxyl group of 1 to 6 carbons; $R_4$ is an alkyl group of 1 to 3 carbons, phenyl or tolyl; and Ar is an aryl group of 7 to 20 carbons or a heterocyclic group.

In the present invention, illustrative examples of the alkyl groups of 1 to 6 carbons include methyl, ethyl, propyl, isopropyl, n-butyl, iso-butyl, s-butyl, t-butyl, pentyl, isopentyl, neopentyl, hexyl and cyclohexyl. Some or all of the hydrogens may be substituted with, for example, halogen atoms such as fluorine, chlorine, bromine or iodine, or with alkyl groups of 1 to 3 carbon atoms.

In the invention, illustrative examples of the alkoxy group of 1 to 6 carbons include methoxy, ethoxy, n-propoxy, isopropoxy, n-butoxy, iso-butoxy, s-butoxy, t-butoxy, pentyloxy, isopentyloxy, neopentyloxy, hexyloxy and cyclohexyloxy. Some or all of the hydrogens may be substituted with, for example, halogen atoms such as fluorine, chlorine, bromine or iodine, or with alkyl groups of 1 to 3 carbon atoms.

Moreover, in the present invention, it is preferable for at least two from among $R_1$, $R_2$ and $R_3$ to be hydrogen atoms or methyl groups, and it is more preferable for $R_1$, $R_2$ and $R_3$ to be hydrogen atoms.

$R_4$ is an alkyl group of 1 to 3 carbons, examples of which include methyl, ethyl, propyl and isopropyl, or is phenyl or tolyl. Some or all of the hydrogen atoms may be substituted with, for example, halogen atoms such as fluorine, chlorine, bromine or iodine. It is especially preferable for $R_4$ to be methyl.

Also, in the present invention, illustrative examples of the aryl groups of 7 to 20 carbons include naphthyl, biphenyl, anthryl and phenanthryl. Some or all of the hydrogens may be substituted with, for example, halogen atoms such as fluorine, chlorine, bromine or iodine, or with alkyl groups of 1 to 3 carbon atoms.

In addition, in the present invention, illustrative examples of the heterocyclic groups include furyl, thienyl, pyridyl, piperidyl, quinolyl and isoquinolyl.

Also, in the present invention, Ar is preferably of one type selected from the group consisting of naphthyl, biphenyl, anthryl, tolyl, xylyl and phenanthryl. It is especially preferable for Ar to be anthryl.

Illustrative examples of above Compound (I) include Compounds (I-1) to (I-108) shown in Tables 1 to 4 below. In Tables 1 to 4, H represents a hydrogen atom, Me is a methyl group, Et is an ethyl group, and *1 to *10 represent substituents having the following structures.

TABLE 1

| Compound No. | R₁ | R₂ | R₃ | R₄ | Ar |
|---|---|---|---|---|---|
| I-1 | H | H | H | Me | *5 |
| I-2 | Me | Me | H | Me | *5 |
| I-3 | Me | Me | Me | Me | *5 |
| I-4 | H | H | H | Et | *5 |
| I-5 | Me | Me | H | Et | *5 |
| I-6 | Me | Me | Me | Et | *5 |
| I-7 | H | H | H | *1 | *5 |
| I-8 | Me | Me | H | *1 | *5 |
| I-9 | Me | Me | Me | *1 | *5 |
| I-10 | H | H | H | *2 | *5 |
| I-11 | Me | Me | H | *2 | *5 |
| I-12 | Me | Me | Me | *2 | *5 |
| I-13 | H | H | H | *3 | *5 |
| I-14 | Me | Me | H | *3 | *5 |
| I-15 | Me | Me | Me | *3 | *5 |
| I-16 | H | H | H | *4 | *5 |
| I-17 | Me | Me | H | *4 | *5 |
| I-18 | Me | Me | Me | *4 | *5 |
| I-19 | H | H | H | Me | *6 |
| I-20 | Me | Me | H | Me | *6 |
| I-21 | Me | Me | Me | Me | *6 |
| I-22 | H | H | H | Et | *6 |
| I-23 | Me | Me | H | Et | *6 |
| I-24 | Me | Me | Me | Et | *6 |
| I-25 | H | H | H | *1 | *6 |
| I-26 | Me | Me | H | *1 | *6 |
| I-27 | Me | Me | Me | *1 | *6 |
| I-28 | H | H | H | *2 | *6 |
| I-29 | Me | Me | H | *2 | *6 |
| I-30 | Me | Me | Me | *2 | *6 |

*1 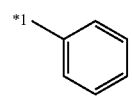

*2 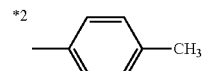

*3 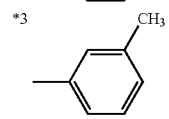

*4 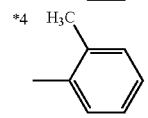

*5 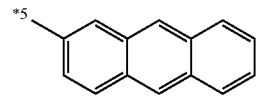

*6 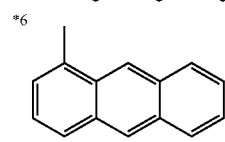

*7 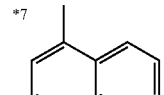

*8 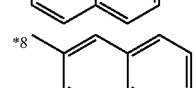

*9 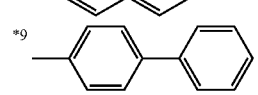

*10

TABLE 2

| Compound No. | R₁ | R₂ | R₃ | R₄ | Ar |
|---|---|---|---|---|---|
| I-31 | H | H | H | *3 | *6 |
| I-32 | Me | Me | H | *3 | *6 |
| I-33 | Me | Me | Me | *3 | *6 |
| I-34 | H | H | H | *4 | *6 |
| I-35 | Me | Me | H | *4 | *6 |
| I-36 | Me | Me | Me | *4 | *6 |
| I-37 | H | H | H | Me | *7 |
| I-38 | Me | Me | H | Me | *7 |
| I-39 | Me | Me | Me | Me | *7 |
| I-40 | H | H | H | Et | *7 |
| I-41 | Me | Me | H | Et | *7 |
| I-42 | Me | Me | Me | Et | *7 |
| I-43 | H | H | H | *1 | *7 |
| I-44 | Me | Me | H | *1 | *7 |
| I-45 | Me | Me | Me | *1 | *7 |
| I-46 | H | H | H | *2 | *7 |
| I-47 | Me | Me | H | *2 | *7 |
| I-48 | Me | Me | Me | *2 | *7 |
| I-49 | H | H | H | *3 | *7 |
| I-50 | Me | Me | H | *3 | *7 |
| I-51 | Me | Me | Me | *3 | *7 |
| I-52 | H | H | H | *4 | *7 |
| I-53 | Me | Me | H | *4 | *7 |
| I-54 | Me | Me | Me | *4 | *7 |
| I-55 | H | H | H | Me | *8 |
| I-56 | Me | Me | H | Me | *8 |
| I-57 | Me | Me | Me | Me | *8 |
| I-58 | H | H | H | Et | *8 |
| I-59 | Me | Me | H | Et | *8 |
| I-60 | Me | Me | Me | Et | *8 |

TABLE 3

| Compound No. | R₁ | R₂ | R₃ | R₄ | Ar |
|---|---|---|---|---|---|
| I-61 | H | H | H | *1 | *8 |
| I-62 | Me | Me | H | *1 | *8 |
| I-63 | Me | Me | Me | *1 | *8 |
| I-64 | H | H | H | *2 | *8 |
| I-65 | Me | Me | H | *2 | *8 |
| I-66 | Me | Me | Me | *2 | *8 |
| I-67 | H | H | H | *3 | *8 |
| I-68 | Me | Me | H | *3 | *8 |
| I-69 | Me | Me | Me | *3 | *8 |
| I-70 | H | H | H | *4 | *8 |
| I-71 | Me | Me | H | *4 | *8 |
| I-72 | Me | Me | Me | *4 | *8 |
| I-73 | H | H | H | Me | *9 |
| I-74 | Me | Me | H | Me | *9 |
| I-75 | Me | Me | Me | Me | *9 |
| I-76 | H | H | H | Et | *9 |
| I-77 | Me | Me | H | Et | *9 |
| I-78 | Me | Me | Me | Et | *9 |
| I-79 | H | H | H | *1 | *9 |
| I-80 | Me | Me | H | *1 | *9 |
| I-81 | Me | Me | Me | *1 | *9 |

TABLE 3-continued

| Compound | Group in general formula (I) | | | | |
|---|---|---|---|---|---|
| No. | $R_1$ | $R_2$ | $R_3$ | $R_4$ | Ar |
| I-82 | H | H | H | *2 | *9 |
| I-83 | Me | Me | H | *2 | *9 |
| I-84 | Me | Me | Me | *2 | *9 |
| I-85 | H | H | H | *3 | *9 |
| I-86 | Me | Me | H | *3 | *9 |
| I-87 | Me | Me | Me | *3 | *9 |
| I-88 | H | H | H | *4 | *9 |
| I-89 | Me | Me | H | *4 | *9 |
| I-90 | Me | Me | Me | *4 | *9 |

TABLE 4

| Compound | Group in general formula (I) | | | | |
|---|---|---|---|---|---|
| No. | $R_1$ | $R_2$ | $R_3$ | $R_4$ | Ar |
| I-91 | H | H | H | Me | *10 |
| I-92 | Me | Me | H | Me | *10 |
| I-93 | Me | Me | Me | Me | *10 |
| I-94 | H | H | H | Et | *10 |
| I-95 | Me | Me | H | Et | *10 |
| I-96 | Me | Me | Me | Et | *10 |
| I-97 | H | H | H | *1 | *10 |
| I-98 | Me | Me | H | *1 | *10 |
| I-99 | Me | Me | Me | *1 | *10 |
| I-100 | H | H | H | *2 | *10 |
| I-101 | Me | Me | H | *2 | *10 |
| I-102 | Me | Me | Me | *2 | *10 |
| I-103 | H | H | H | *3 | *10 |
| I-104 | Me | Me | H | *3 | *10 |
| I-105 | Me | Me | Me | *3 | *10 |
| I-106 | H | H | H | *4 | *10 |
| I-107 | Me | Me | H | *4 | *10 |
| I-108 | Me | Me | Me | *4 | *10 |

In the present invention, Compound (I) is prepared, for example, in the following way.

Step (a): As shown in Reaction Formula 1 below, Compound 1, a ketone compound (A), 2-(dicyclohexylphosphino)biphenyl (DCHPBP), tris(dibenzylidene acetone) dipalladium (a palladium catalyst, abbreviated as "Pd cat.") and t-BuONa were reacted to obtain Compound 2.

Reaction Formula 1:

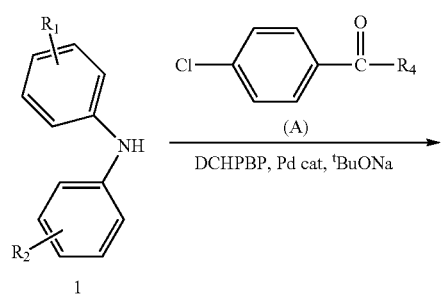

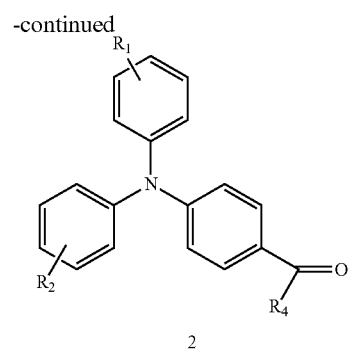

Step (b): As shown in Reaction Formula 2 below, Compound 3 and an aldehyde ($R_3$PhCHO) were reacted in a solvent (tetrahydrofuran, THF) and in the presence of a catalyst (n-BuLi) to form Compound 4, which was then purified by extraction.

Reaction Formula 2:

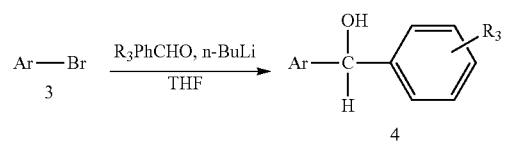

Step (c): As shown in Reaction Formula 3 below, Compound 4 and phosphorus tribromide were reacted in a solvent ($CH_2Cl_2$) to form Compound 5.

Reaction Formula 3:

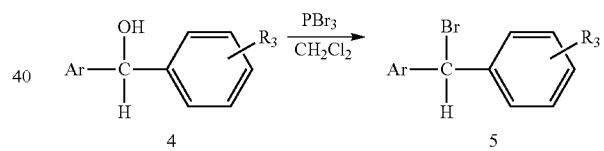

Step (d): As shown in Reaction Formula 4 below, Compound 5 and $NaIO_4$-DMF (dimethylformamide) were reacted to form Compound 6, which was then purified by extraction.

Reaction Formula 4:

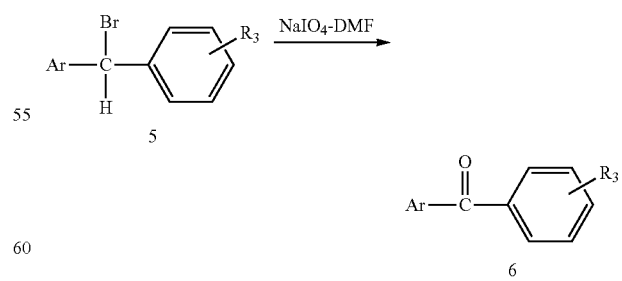

Step (e): As shown in Reaction Formula 5 below, Compound 6 and Compound 2 were reacted in a solvent and in the presence of a catalyst to form Compound (I) (McMurry reaction), which was then purified by extraction.

Reaction Formula 5:

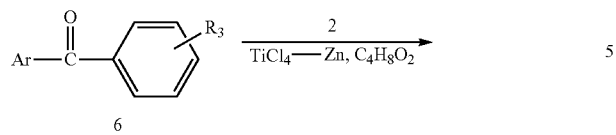

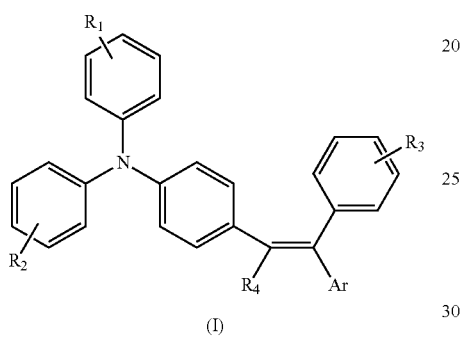

Compound (I) synthesized in the present invention is sometimes obtained as a mixture of the E-form and the Z-form. In such cases, by dissolving the mixture in a solvent in which the solubilities of the E-form and the Z-form differ, it is possible to isolate the E-form alone or the Z-form alone. Isolation by column purification is also possible.

In Reaction Formula 5, the reaction proportions (molar ratio) between Compound 2 and Compound 6 are preferably 1:1. If the amount of Compound 2 is too small, the yield of Compound (I) may worsen. On the other hand, if the amount of Compound 2 is too large, the amount of unreacted Compound 2 will increase, as a result of which Compound (I) may be difficult to purify.

Also, the reaction temperature is preferably from −20 to 100° C., and the reaction time is preferably from 2 to 8 hours. By setting these conditions within the above ranges, the desired reaction can be effectively carried out with a relatively simple production set-up.

In addition, illustrative examples of the catalyst include titanium tetrachloride-zinc, titanium trichloride-aluminum hydride, titanium trichloride-zinc, titanium trichloride-copper, and titanium trichloride-lithium. A single catalyst may be used alone, or a combination of two or more catalysts may be used together.

The catalyst is added in an amount of preferably from 1 to 1.5 moles per mole of Compound 6. With the addition of less than 1 mole of the catalyst, the reactivity of Compound 2 with Compound 6 may markedly decrease. With the addition of more than 1.5 moles of the catalyst, the reaction of Compound 2 and Compound 6 may be difficult to control.

Compounds 1-1 to 1-10 having the following formulas are preferred as Compound 1 in Reaction Formula 1. Compounds 1-1 and Formula 1-2 are more preferred.

1-1
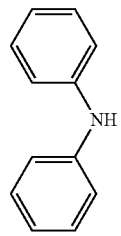

1-2
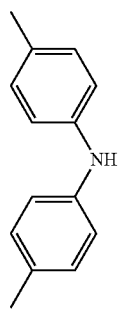

1-3
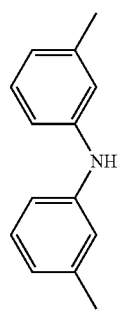

1-4
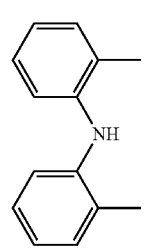

1-5
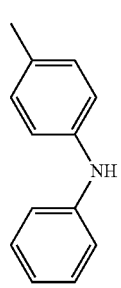

13
-continued 1-6

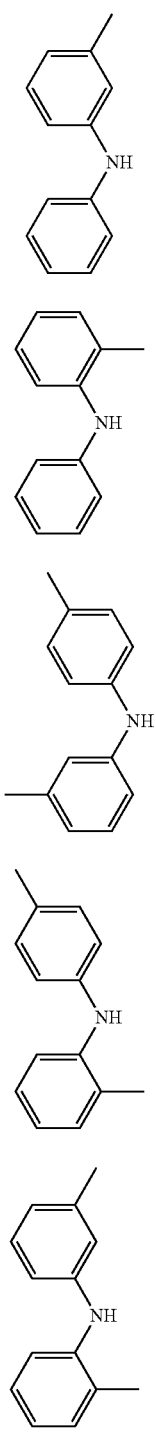

1-7

1-8

1-9

1-10

Compounds A-1 to A-6 having the following formulas are preferred as Compound (A) in Reaction Formula 1.

A-1

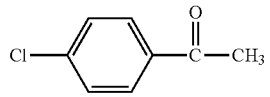

14
-continued

A-2

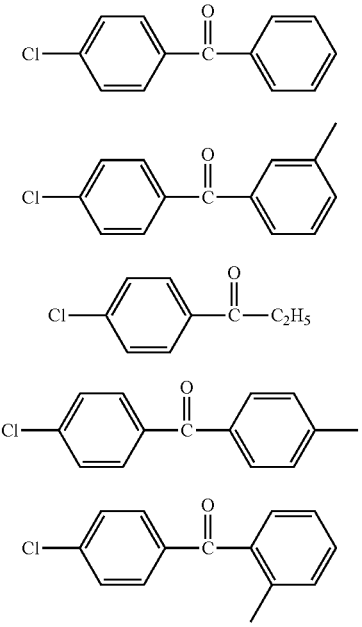

A-3

A-4

A-5

A-6

Compounds 3-1 to 3-6 of the following formulas are preferred as Compound 3 in Reaction Formula 2.

3-1

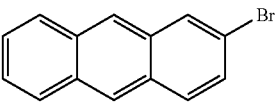

3-2

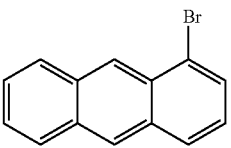

3-3

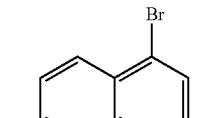

3-4

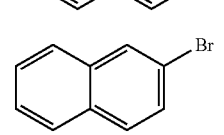

3-5

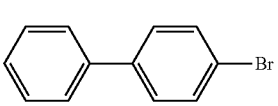

3-6

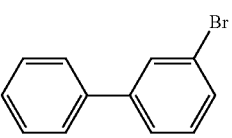

In addition, Compounds R3-1 to R3-4 of the following formulas are preferred as the aldehyde compound ($R_3PhCHO$) of Reaction Formula 2. Compounds R3-1 and R3-2 are more preferred.

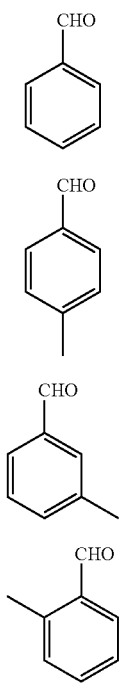

R3-1
R3-2
R3-3
R3-4

The charge transport material of the present invention includes the ethylene compound of above general formula (I) (Compound (I)).

Electrophotographic Photoreceptor

The electrophotographic photoreceptor of the present invention is an electrophotographic photoreceptor having a conductive substrate and at least a photosensitive layer on the conductive substrate, which photosensitive layer includes an ethylene compound of above general formula (I) (Compound (I)).

The electrophotographic photoreceptor of the invention is exemplified by, based on the layer construction of the photosensitive layer: (i) single layer type photoreceptors and (ii) multi layer photoreceptors. These photoreceptors may be used as either positive-charging or negative-charging photoreceptors. Also, the photosensitive layer includes at least a charge transport material, and preferably includes also a charge generation material and a resin binder.

Single Layer Type Photoreceptor

FIG. 1 is a schematic cross-sectional diagram showing an example of a single layer type photoreceptor. The single layer type photoreceptor 110 has a conductive substrate 10, an undercoat layer 20 provided on the conductive substrate 10, and a photosensitive layer 30 containing a charge generation material, a charge transport material and a resin binder.

Illustrative examples of the conductive substrate 10 include metals such as iron, aluminum, copper, tin, platinum, silver, vanadium, molybdenum, chromium, cadmium, titanium, nickel, palladium, indium, stainless steel and brass; plastic materials on which a metal has been vapor-deposited or laminated; and glass coated with aluminum iodide, tin oxide, indium oxide or the like. The shape of the conductive substrate is exemplified by sheet-like and drum-like shapes. The shape of the conductive substrate 10 may be selected as appropriate for the structure of the image-forming device.

The undercoat layer 20, which is a layer composed primarily of resin or is made of a metal oxide (e.g., Alumite) film, is provided as needed in order to control charge injectability from the conductive substrate 10 to the photosensitive layer 30, or for the purpose of, e.g., covering defects in the substrate surface and enhancing adhesion between the photosensitive layer 30 and the underlying material. Illustrative examples of resin materials that may be used in the undercoat layer 20 include insulating polymers such as casein, polyvinyl alcohol, polyamide, melamine and cellulose; and conductive polymers such as polythiophene, polypyrrole and polyaniline. These resins may be used singly or may be suitably combined and used in admixture. Alternatively, these resins may include metal oxides such as titanium dioxide and zinc oxide.

The photosensitive layer 30 is formed by, for example, applying onto the conductive substrate 10 then drying a liquid coating prepared by dissolving or dispersing in a solvent at least a charge transport material containing Compound (I), a charge generation material and a resin binder, and also, optionally, an electron (charge) transporting agent. Preparation of the liquid coating is carried out by using, for example, a roll mill, ball mill, attritor, paint shaker or ultrasonic disperser to dissolve or disperse each of the ingredients in the solvent. A known method may be used as the coating method. The charge transport material containing Compound (I) is sometimes referred to below as a "hole transporting agent."

The photosensitive layer 30 has a thickness of preferably from 5 to 100 μm, and more preferably from 10 to 50 μm. At a photosensitive layer 30 thickness outside of this range, the effects are sometimes insufficient and fall short of what is desired.

In the photosensitive layer 30, compound (I) may be used alone as the hole transporting agent, or may be suitably combined and used in admixture with, e.g., a hydrazone compound, a butadiene compound, a diamine compound, an indole compound, an indoline compound, a stilbene compound or a distilbene compound. In the photosensitive layer 30, either a Z-form or an E-form of Compound (I) may be used primarily or exclusively, or both may be used in admixture. The content of the hole transporting agent, based on the solids content of the single layer type photosensitive layer 30, is preferably from 1 to 50 wt %, and more preferably from 3 to 40 wt %.

Illustrative examples of the electron transporting agent used in the photosensitive layer 30 include succinic anhydride, maleic anhydride, dibromosuccinic anhydride, phthalic anhydride, 3-nitrophthalic anhydride, 4-nitrophthalic anhydride, pyromellitic anhydride, pyromellitic acid, trimellitic acid, trimellitic anhydride, phthalimide, 4-nitrophthalimide, tetracyanoethylene, tetracyanoquinodimethane, chloranil, bromanil, o-nitrobenzoic acid, malononitrile, trinitrofluorenone, trinitrothioxanthone, dinitrobenzene, dinitroanthracene, dinitroacridine, nitroanthraquinone, dinitroanthraquinone, thiopyran compounds, quinone compounds, benzoquinone compounds, diphenoquinone compounds, naphthoquinone compounds, anthraquinone compounds, stilbenequinone compounds and azoquinone compounds. These electron transporting agents may be used singly or as combinations or two or more thereof. The content of the electron transporting agent, based on the solids content of the single-layer photosensitive layer 30, is preferably from 1 to 50 wt %, and more preferably from 3 to 40 wt %.

Titanyl phthalocyanine, a metal-free phthalocyanine pigment or the like may be used singly or as a combination of two or more thereof as the charge generation material.

Illustrative examples of the resin binder include thermoplastic resins such as bisphenol Z, bisphenol ZC, bisphenol C and bisphenol A type polycarbonate resins, polyarylate resins, styrene-butadiene copolymers, styrene-acrylonitrile copolymers, styrene-maleic acid copolymers, acrylic copolymers, styrene-acrylic acid copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, polyurethane resins, polysulfone resins, diallyl phthalate resins, ketone resins, polyvinyl butyral resins, and polyether resins; thermoset resins such as silicone resins, epoxy resins, phenolic resins, urea resins and melamine resins; and photocurable resins such as epoxy acrylates and urethane acrylates. Any one of these may be used alone or combinations of two or more may be used together as the resin binder.

The photosensitive layer 30 may include known additives, within a range that does not adversely impact the electrophotographic properties. Examples of such additives include deterioration inhibitors such as antioxidants, radical scavengers, singlet quenchers and ultraviolet absorbers, and also softeners, plasticizers, surface modifiers, extenders, thickeners, dispersion stabilizers, waxes, acceptors and donors. To enhance the sensitivity of the photosensitive layer 30, a known sensitizer such as terphenyl, halonaphthoquinones or acenaphthylene may be used together with the charge generation material.

Illustrative examples of solvents for dissolving or dispersing the above materials and preparing a liquid coating include alcohols such as methanol, ethanol, isopropanol and butanol; aliphatic hydrocarbons such as n-hexane, octane and cyclohexane; aromatic hydrocarbons such as benzene, toluene and xylene; halogenated hydrocarbons such as dichloromethane, dichloroethane, chloroform, carbon tetrachloride and chlorobenzene; ethers such as dimethyl ether, diethyl ether, tetrahydrofuran, ethylene glycol dimethyl ether and diethylene glycol dimethyl ether; ketones such as acetone, methyl ethyl ketone and cyclohexanone; esters such as ethyl acetate and methyl acetate; and dimethyl formaldehyde, dimethyl formamide and dimethyl sulfoxide. Any one of these may be used alone or combinations of two or more may be used together as the solvent. To improve the dispersibility of the various ingredients and enhance the smoothness of the photosensitive layer surface, a surfactant, leveling agent and the like may be added to the liquid coating.

Negative-Charging Multi Layer Photoreceptor

Figure 2:
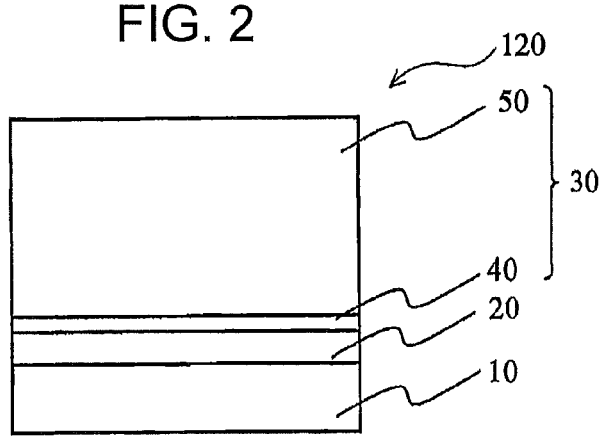
FIG. 2 is a schematic cross-sectional diagram showing an example of a negative-charging multi layer photoreceptor.

FIG. 2 is a schematic cross-sectional diagram showing an example of a negative-charging multi layer photoreceptor. The negative-charging multi layer photoreceptor 120 has a conductive substrate 10, an undercoat layer 20 provided on the conductive substrate 10, a charge generation material-containing charge generation layer 40, and a charge transport layer 50 provided on the charge generation layer 40. Here, the photosensitive layer 30 is constructed by successively laminating the charge generation layer 40 and the charge transport layer 50.

The conductive substrate 10 and the undercoat layer 20 used here may be of the same type as those used in the single layer type photoreceptor 110.

The charge generation layer 40 includes a charge generation material and a resin binder. The charge generation material may be either titanyl phthalocyanine or metal-free phthalocyanine, or both may be used. The resin binder used is not subject to any particular limitation, and may be the same resin binder as that described above. A suitable resin binder may be selected from among various polyvinyl chloride, polyvinyl butyral, polyvinyl acetal, polyester, polycarbonate, acrylic resins and phenoxy resins. The film thickness of the charge generation layer 40 is preferably from 0.1 to 5 µm, and more preferably from 0.2 to 0.5 µm.

The charge transport layer 50 includes a charge transport material and a resin binder. Compound (I) may be used alone as the charge transport material, or may be suitably combined and used in admixture with, e.g., a hydrazone compound, butadiene compound, diamine compound, indole compound, indoline compound, stilbene compound or distilbene compound. The bonding resin may be a polycarbonate resin (e.g., bisphenol A, bisphenol Z, or bisphenol A-biphenyl copolymer), polystyrene resin or polyphenylene resin, any of these being used alone or mixed and used together in a suitable combination. In the charge transport layer 50, either a Z-form or an E-form of Compound (I) may be used primarily or exclusively, or both may be used in admixture. The content of the charge transport material, based on the solids content of the charge transport layer 50, is preferably from 10 to 90 wt %, and more preferably from 20 to 80 wt %. To maintain a practically effective surface potential, the film thickness of the charge transport layer 50 is in a range of preferably from 3 to 50 µm, and more preferably from 15 to 40 µm.

In addition, electron accepting materials, antioxidants, light stabilizers and the like may be added to the undercoat layer 20 and the charge transport layer 50 where necessary so as to, for example, enhance sensitivity, reduce the residual potential, or improve the environmental resistance and the stability to harmful light. Illustrative, non-limiting, examples of compounds that may be used for such purposes include coumarol derivatives of tocopherol and the like, ether compounds, ester compounds, polyarylalkane compounds, hydroquinone derivatives, diether compounds, benzophenone derivative, benzotriazole derivatives, thioether compounds, phenylenediamine derivatives, phosphonic acid esters, phosphorous acid esters, phenol compounds, hindered phenol compounds, linear amine compounds, cyclic amine compounds and hindered amine compounds.

In addition, leveling agents such as silicone oils or fluorine-containing oils may be included in the photosensitive layer 30 for the purpose of enhancing the leveling properties of the formed film and imparting further lubricity.

If necessary, a surface protecting layer may additionally be provided on the surface of the photosensitive layer 30 to further enhance the environmental resistance and mechanical strength. The surface protecting layer is made of a material having excellent durability to mechanical stress and excellent environmental resistance, and is desired because it has the ability to allow light to which the charge generation layer 40 responds to pass therethrough with minimal loss.

The undercoat layer 20 is formed by a means of application such as coating similar to that used for the photosensitive layer 30 on a single layer type photoreceptor 110. Further, the charge generation layer 40 is formed by a means such as vapor deposition or coating. Moreover, the charge transport layer 50 is formed by a means of application such as coating similar to that used for the photosensitive layer 30 on a single layer type photoreceptor 110.

Positive-Charging Multi layer Photoreceptor

Figure 3:
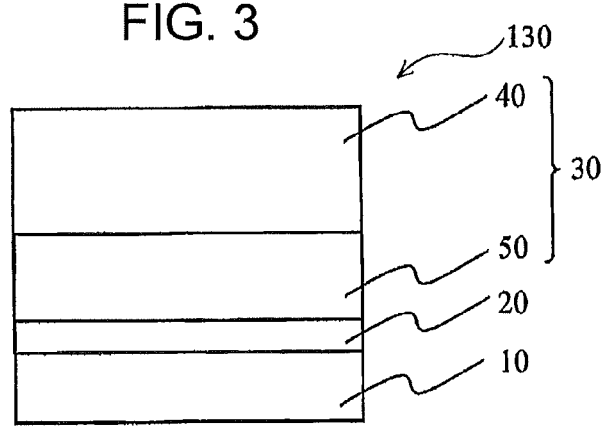
FIG. 3 is a schematic cross-sectional diagram showing an example of a positive-charging multi layer photoreceptor.

FIG. 3 is a schematic cross-sectional diagram showing an example of a positive-charging multi layer photoreceptor. The positive-charging multi layer photoreceptor 130 has a conductive substrate 10, an undercoat layer 20 provided on the conductive substrate 10, a charge transport layer 50, and a charge generation material-containing charge generation layer 40 provided on the charge transport layer 50. Here, the photosensitive layer 30 is constructed by successively laminating the charge transport layer 50 and the charge generation layer 40.

In the positive-charging multi layer photoreceptor 130, the charge transport layer 50 is composed primarily of a charge transport material and a resin binder. The same materials as those mentioned above in connection with the embodiment of a charge transport layer 50 in a negative-charging multi layer photoreceptor 120 may be used as the charge transport material and resin binder. The contents of the respective materials and the film thickness of the charge transport layer 50 may be made the same as in a negative-charging multi layer photoreceptor 120.

The charge generation layer 40 provided on the charge transport layer 50 is composed primarily of a charge generation material, a hole transporting agent, an electron transporting agent (acceptor-type compound), and a resin binder. The same materials as those mentioned above in connection with an embodiment of a single layer type photosensitive layer 30 in a single layer type photoreceptor 110 may be used as the charge generation material, the hole transporting agent, the electron transporting agent and the resin binder. The contents of the respective materials may be made similar to the amounts mentioned in the embodiment of a single layer type photosensitive layer 30 in the single layer type photoreceptor 110. The film thickness of the charge generation layer 40 is preferably in a range of from 3 to 50 µm, and more preferably from 8 to 35 µm.

Three types of photosensitive layers have been described above as embodiments. However, the photosensitive layer of the invention is not limited to these layer constructions, and encompasses also constructions in which other functional layers are added.

EXAMPLES

Next, the present invention is illustrated more fully by working examples. However, the invention is not limited by the following preparation examples and working examples, provided it is practiced in a manner that does not depart from the spirit and scope thereof. In the examples, parts are given by weight.

Preparation of Example 1

Preparation of Compound I-1

Step (a): A 2-liter, two-neck flask was charged with Compound 11 below (25.5 g, 0.15 mol), 1-(4-chlorophenyl)ethanone (23.3 g, 0.15 mol), 2-(dicyclohexylphosphino)biphenyl (0.13 g, 0.038 mmol), trisdibenzylidene acetone dipalladium (0.17 g, 0.19 mmol), t-BuONa (15.4 g, 0.16 mol) and 500 mL of o-xylene. The system was then flushed with argon and the flask contents were stirred at 120° C. for 5 hours, following which the system was cooled to room temperature. The organic phase within the reaction mixture was washed three times with ion-exchanged water, following which anhydrous sodium sulfate and activated clay were added to the organic phase, and drying and adsorption treatment carried out. The xylene was then driven off by vacuum distillation. The resulting residue was purified by column chromatography (chloroform/hexane development), giving Compound 12 below as a solid (yield by weight, 37.02 g; percent yield, 86%).

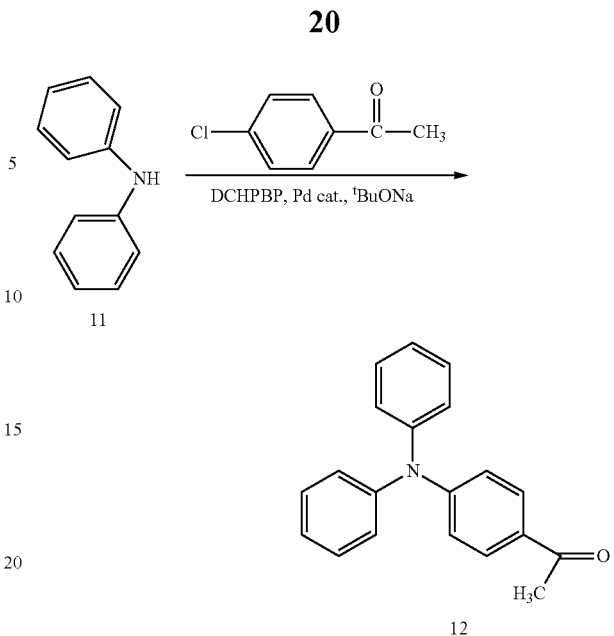

Step (b): A 2-liter flask was charged with Compound 13 below (16.2 g, 0.063 mol), nBuLi (27.7 mL, 0.07 mol) and 500 mL of tetrahydrofuran (THF). The system was then flushed with argon and the flask contents were stirred at −78° C. for 30 minutes. Benzaldehyde (PhCHO) (9.60 g, 0.09 mol) was then added and the flask contents were again stirred for 1 hour. After stirring, the temperature of the reaction mixture was raised to −30° C., following which an aqueous solution of aluminum chloride was added, isopropyl acetate (IPAC) was added to standard temperature, and anhydrous sodium sulfate was added to the organic phase. The residue thus obtained was purified by column chromatography, giving Compound 14 below as a solid (yield by weight, 11.4 g; percent yield, 63%)

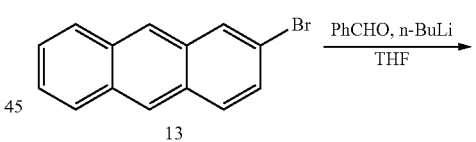

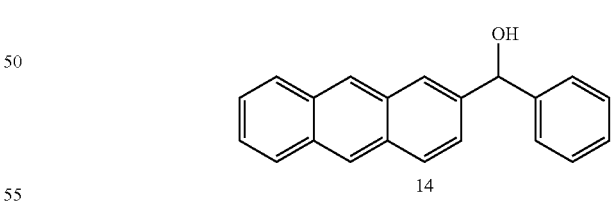

Step (c): A 2-liter flask was charged with Compound 14 (11.4 g, 0.039 mol) and 400 mL of dichloromethane, flushed with argon, and the flask contents were stirred at −25° C. for 15 minutes. Phosphorus tribromide (4.25 g, 0.016 mol) was then added and the flask contents were again stirred for 3 hours. Water and dichloromethane were added to the reaction mixture, then anhydrous sodium sulfate was added to the organic phase and purification was carried out, giving Compound 15 below as a solid (yield by weight, 12.69 g; percent yield, 93%).

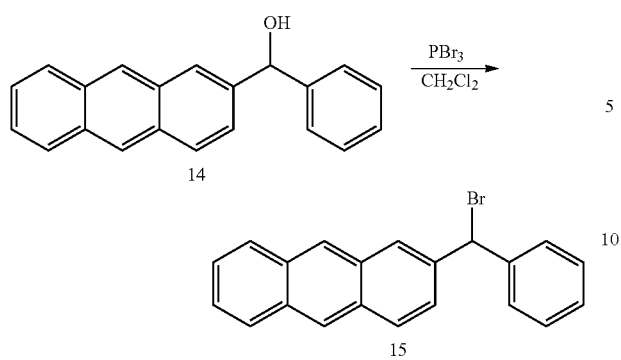

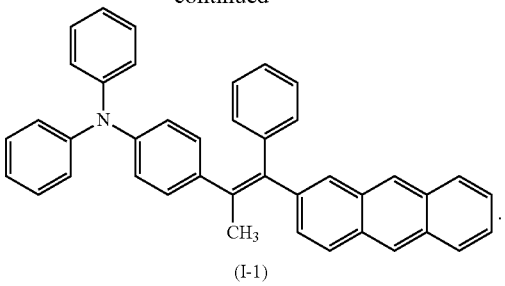

Step (d): A 2-liter flask was charged with Compound 15 (12.69 g, 0.037 mol), NaIO₄ (7.92 g, 0.037 mol) and 500 mL of dimethylformamide (DMF), and the flask contents were stirrer at 150° C. for 5 hours. Ether and water were then added to the reaction mixture, following which anhydrous sodium sulfate was added to the organic phase and the ether was removed by distillation. The residue thus obtained was purified with a column, thereby giving Compound 16 below as a solid (yield by weight, 8.27 g; percent yield, 80%).

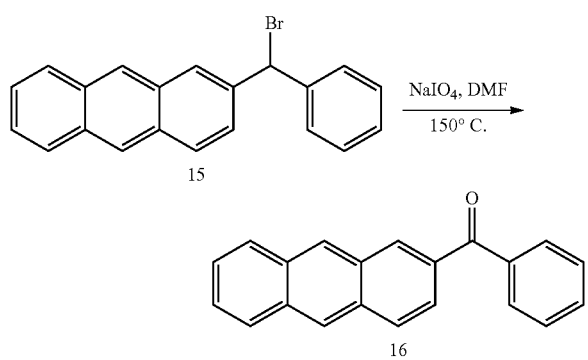

Step (e): A 2-liter, three-neck flask was charged with Compound 16 (8.27 g, 0.029 mol) and Compound 12 (8.32 g, 0.029 mol), then flushed with argon. Next, 200 mL of dried dioxane and titanium tetrachloride (3.82 mL, 0.035 mol) were added, and the flask contents were stirred at room temperature for 30 minutes. After stirring, zinc (3.77 g, 0.058 mol) was added and the flask contents were stirred for 2 hours, following which the flask contents were reacted for 3 hours up to 100° C. The organic phase within the reaction mixture was subsequently washed three times with ion-exchanged water, then extracted with ether, following which anhydrous sodium sulfate was added to the organic phase and the ether was driven off by vacuum distillation. The resulting product was purified by recrystallization from ethyl acetate/hexane, giving Compound (I-1) as a solid (yield by weight, 6.38 g; percent yield, 41%).

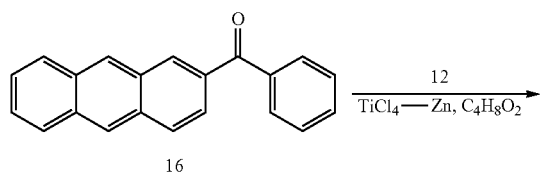

The analytic results obtained for Compound (I-1) are shown below.

Figure 4:
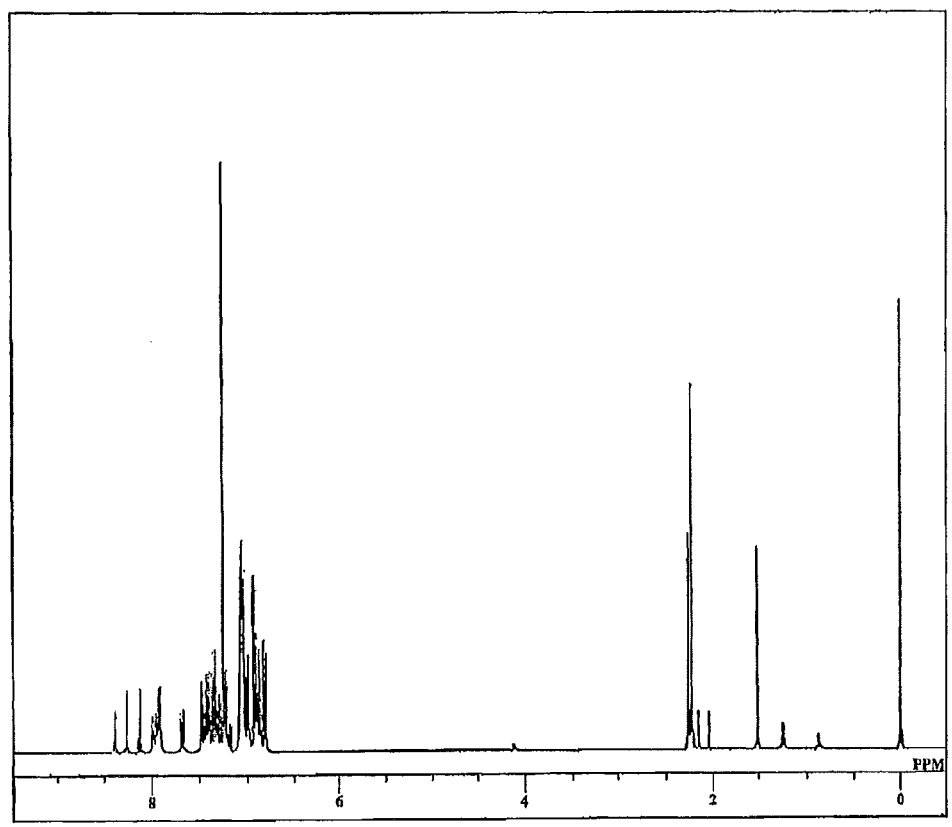
FIG. 4 is an NMR chart of Compound (I-1).

(1) NMR Analysis Results (E/Z=58/42):

FIG. 4 shows the NMR chart for Compound (I-1). The signals for Compound (I-1) are shown below.

$^1$H-NMR (CDCl$_3$; 400 MHz); δ8.41 (0.58H, s, Ar—H for E), δ8.39 (0.42H, s, Ar—H for Z), δ8.28 (0.58H, s, Ar—H for E), δ8.14 (0.42H, s, Ar—H for Z), 68.01-7.91 (3H, m, Ar—H for E and Z), δ7.69-7.13 (10H, m Ar—H (for E and Z), δ7.11-6.79 (13H, m, Ar—H for E and Z), δ2.26 (1.74H, s, CH$_3$ for E), δ2.23 (1.26H, s, CH$_3$ for Z).

(2) Mass Analysis Results: m/e=537 (calculated, 537).

Preparation of Example 2

In Step (e) for the ethylene compound (No. I-1) in Preparation Example 1, the reaction of Compound 16 with Compound 12 according to the synthesis method described in Japanese Patent Application Laid-open No. S60-104951 was attempted, but the target product was not obtained.

Production of Negative-Charging Multi layer Photoreceptors:

Working Example 1

A liquid coating was prepared by dissolving and dispersing 5 parts by weight of an alcohol-soluble nylon (CM 8000 (trade name), available from Toray Industries, Inc.) and 5 parts by weight of aminosilane-treated titanium oxide fine particles in 90 parts by weight of methanol. An aluminum cylinder having an outside diameter of 24 mm was used as the conductive substrate. The liquid coating was dip-coated as the undercoat layer onto the outer periphery of the aluminum cylinder, then dried at a temperature of 100° C. for 30 minutes to form an undercoat layer having a film thickness of about 2 μm.

Next, a slurry was prepared by dissolving 1 part by weight of polyvinyl butyral resin in 98 parts by weight of dichloromethane, and adding thereto 2 parts by weight of α-type titanyl phthalocyanine. Using a disk-type bead mill filled with zirconia beads having a bead diameter of 0.4 μm to a bulk filling fraction based on the vessel volume of 85 v/v %, 5 liters of the slurry was subjected to 10 treatment passes at a treatment liquid flow rate of 300 mL and a disk peripheral speed of 3 m/s, thereby preparing a charge generation layer-forming liquid coating.

The resulting charge generation layer-forming liquid coating was used to form a charge generation layer on the conductive substrate on which the undercoat layer had been formed. Drying was then carried out at a drying temperature of 80° C. and a drying time of 30 minutes. The resulting charge generation layer had a film thickness after drying of from 0.1 to 0.5 μm.

A liquid coating prepared by dissolving 9 parts by weight of an ethylene compound (No. I-1) as the charge transport material and 11 parts by weight of a polycarbonate resin (Toughzet B-500 (trade name), available from Idemitsu Kosan Co., Ltd.) as the resin binder in 80 parts by weight of dichloromethane was dip-coated onto this charge generation layer. The coating was then dried at a temperature of 90° C. for 60 minutes to form a 25 μm charge transport layer, thereby completing production of an electrophotographic photoreceptor.

Working Example 2

Aside from using ethylene compound No. I-2 (wherein $R_1$ and $R_2$ are at para positions) instead of the ethylene compound (No. I-1) used in Working Example 1, an electrophotographic photoreceptor was produced by exactly the same method.

Working Example 3

Aside from using ethylene compound No. I-3 (wherein $R_1$, $R_2$ and $R_3$ are at para positions) instead of the ethylene compound (No. I-1) used in Working Example 1, an electrophotographic photoreceptor was produced by exactly the same method.

Working Example 4

Aside from using ethylene compound No. I-4 instead of the ethylene compound (No. I-1) used in Working Example 1, an electrophotographic photoreceptor was produced by exactly the same method.

Working Example 5

Aside from using ethylene compound No. I-5 (wherein $R_1$ and $R_2$ are at para positions) instead of the ethylene compound (No. I-1) used in Working Example 1, an electrophotographic photoreceptor was produced by exactly the same method.

Working Example 6

Aside from using ethylene compound No. I-6 (wherein $R_1$, $R_2$ and $R_3$ are at para positions) instead of the ethylene compound (No. I-1) used in Working Example 1, an electrophotographic photoreceptor was produced by exactly the same method.

Working Example 7

Aside from using ethylene compound No. I-7 instead of the ethylene compound (No. I-1) used in Working Example 1, an electrophotographic photoreceptor was produced by exactly the same method.

Working Example 8

Aside from using ethylene compound No. I-8 (wherein $R_1$ and $R_2$ are at para positions) instead of the ethylene compound (No. I-1) used in Working Example 1, an electrophotographic photoreceptor was produced by exactly the same method.

Working Example 9

Aside from using ethylene compound No. I-9 (wherein $R_1$, $R_2$ and $R_3$ are at para positions) instead of the ethylene compound (No. I-1) used in Working Example 1, an electrophotographic photoreceptor was produced by exactly the same method.

Working Example 10

Aside from using ethylene compound No. I-10 instead of the ethylene compound (No. I-1) used in Working Example 1, an electrophotographic photoreceptor was produced by exactly the same method.

Working Example 11

Aside from using ethylene compound No. I-11 (wherein $R_1$ and $R_2$ are at para positions) instead of the ethylene compound (No. I-1) used in Working Example 1, an electrophotographic photoreceptor was produced by exactly the same method.

Working Example 12

Aside from using ethylene compound No. I-12 (wherein $R_1$, $R_2$ and $R_3$ are at para positions) instead of the ethylene compound (No. I-1) used in Working Example 1, an electrophotographic photoreceptor was produced by exactly the same method.

Working Example 13

Aside from using ethylene compound No. I-13 instead of the ethylene compound (No. I-1) used in Working Example 1, an electrophotographic photoreceptor was produced by exactly the same method.

Working Example 14

Aside from using ethylene compound No. I-14 (wherein $R_1$ and $R_2$ are at para positions) instead of the ethylene compound (No. I-1) used in Working Example 1, an electrophotographic photoreceptor was produced by exactly the same method.

Working Example 15

Aside from using ethylene compound No. I-15 (wherein $R_1$, $R_2$ and $R_3$ are at para positions) instead of the ethylene compound (No. I-1) used in Working Example 1, an electrophotographic photoreceptor was produced by exactly the same method.

Working Example 16

Aside from using ethylene compound No. I-16 instead of the ethylene compound (No. I-1) used in Working Example 1, an electrophotographic photoreceptor was produced by exactly the same method.

Working Example 17

Aside from using ethylene compound No. I-17 (wherein $R_1$ and $R_2$ are at para positions) instead of the ethylene compound (No. I-1) used in Working Example 1, an electrophotographic photoreceptor was produced by exactly the same method.

Working Example 18

Aside from using ethylene compound No. I-18 (wherein $R_1$, $R_2$ and $R_3$ are at para positions) instead of the ethylene compound (No. I-1) used in Working Example 1, an electrophotographic photoreceptor was produced by exactly the same method.

Working Example 19

Aside from using ethylene compound No. I-19 instead of the ethylene compound (No. I-1) used in Working Example 1, an electrophotographic photoreceptor was produced by exactly the same method.

Working Example 20

Aside from using ethylene compound No. I-20 (wherein $R_1$ and $R_2$ are at para positions) instead of the ethylene compound (No. I-1) used in Working Example 1, an electrophotographic photoreceptor was produced by exactly the same method.

Working Example 21

Aside from using ethylene compound No. I-21 (wherein $R_1$, $R_2$ and $R_3$ are at para positions) instead of the ethylene compound (No. I-1) used in Working Example 1, an electrophotographic photoreceptor was produced by exactly the same method.

Working Example 22

Aside from using ethylene compound No. I-22 instead of the ethylene compound (No. I-1) used in Working Example 1, an electrophotographic photoreceptor was produced by exactly the same method.

Working Example 23

Aside from using ethylene compound No. I-23 (wherein $R_1$ and $R_2$ are at para positions) instead of the ethylene compound (No. I-1) used in Working Example 1, an electrophotographic photoreceptor was produced by exactly the same method.

Working Example 24

Aside from using ethylene compound No. I-24 (wherein $R_1$, $R_2$ and $R_3$ are at para positions) instead of the ethylene compound (No. I-1) used in Working Example 1, an electrophotographic photoreceptor was produced by exactly the same method.

Working Example 25

Aside from using ethylene compound No. I-25 instead of the ethylene compound (No. I-1) used in Working Example 1, an electrophotographic photoreceptor was produced by exactly the same method.

Working Example 26

Aside from using ethylene compound No. I-26 (wherein $R_1$ and $R_2$ are at para positions) instead of the ethylene compound (No. I-1) used in Working Example 1, an electrophotographic photoreceptor was produced by exactly the same method.

Working Example 27

Aside from using ethylene compound No. I-27 (wherein $R_1$, $R_2$ and $R_3$ are at para positions) instead of the ethylene compound (No. I-1) used in Working Example 1, an electrophotographic photoreceptor was produced by exactly the same method.

Working Example 28

Aside from using ethylene compound No. I-28 instead of the ethylene compound (No. I-1) used in Working Example 1, an electrophotographic photoreceptor was produced by exactly the same method.

Working Example 29

Aside from using ethylene compound No. I-29 (wherein $R_1$ and $R_2$ are at para positions) instead of the ethylene compound (No. I-1) used in Working Example 1, an electrophotographic photoreceptor was produced by exactly the same method.

Working Example 30

Aside from using ethylene compound No. I-30 (wherein $R_1$, $R_2$ and $R_3$ are at para positions) instead of the ethylene compound (No. I-1) used in Working Example 1, an electrophotographic photoreceptor was produced by exactly the same method.

Working Example 31

Aside from using ethylene compound No. I-31 instead of the ethylene compound (No. I-1) used in Working Example 1, an electrophotographic photoreceptor was produced by exactly the same method.

Working Example 32

Aside from using ethylene compound No. I-32 (wherein $R_1$ and $R_2$ are at para positions) instead of the ethylene compound (No. I-1) used in Working Example 1, an electrophotographic photoreceptor was produced by exactly the same method.

Working Example 33

Aside from using ethylene compound No. I-33 (wherein $R_1$, $R_2$ and $R_3$ are at para positions) instead of the ethylene compound (No. I-1) used in Working Example 1, an electrophotographic photoreceptor was produced by exactly the same method.

Working Example 34

Aside from using ethylene compound No. I-34 instead of the ethylene compound (No. I-1) used in Working Example 1, an electrophotographic photoreceptor was produced by exactly the same method.

Working Example 35

Aside from using ethylene compound No. I-35 (wherein $R_1$ and $R_2$ are at para positions) instead of the ethylene compound (No. I-1) used in Working Example 1, an electrophotographic photoreceptor was produced by exactly the same method.

Working Example 36

Aside from using ethylene compound No. I-36 (wherein $R_1$, $R_2$ and $R_3$ are at para positions) instead of the ethylene compound (No. I-1) used in Working Example 1, an electrophotographic photoreceptor was produced by exactly the same method.

Working Example 37

Aside from using ethylene compound No. I-37 instead of the ethylene compound (No. I-1) used in Working Example 1, an electrophotographic photoreceptor was produced by exactly the same method.

Working Example 38

Aside from using ethylene compound No. I-38 (wherein $R_1$ and $R_2$ are at para positions) instead of the ethylene compound (No. I-1) used in Working Example 1, an electrophotographic photoreceptor was produced by exactly the same method.

Working Example 39

Aside from using ethylene compound No. I-39 (wherein $R_1$, $R_2$ and $R_3$ are at para positions) instead of the ethylene compound (No. I-1) used in Working Example 1, an electrophotographic photoreceptor was produced by exactly the same method.

Working Example 40

Aside from using ethylene compound No. I-40 instead of the ethylene compound (No. I-1) used in Working Example 1, an electrophotographic photoreceptor was produced by exactly the same method.

Working Example 41

Aside from using ethylene compound No. I-41 (wherein $R_1$ and $R_2$ are at para positions) instead of the ethylene compound (No. I-1) used in Working Example 1, an electrophotographic photoreceptor was produced by exactly the same method.

Working Example 42

Aside from using ethylene compound No. I-42 (wherein $R_1$, $R_2$ and $R_3$ are at para positions) instead of the ethylene compound (No. I-1) used in Working Example 1, an electrophotographic photoreceptor was produced by exactly the same method.

Working Example 43

Aside from using ethylene compound No. I-43 instead of the ethylene compound (No. I-1) used in Working Example 1, an electrophotographic photoreceptor was produced by exactly the same method.

Working Example 44

Aside from using ethylene compound No. I-44 (wherein $R_1$ and $R_2$ are at para positions) instead of the ethylene compound (No. I-1) used in Working Example 1, an electrophotographic photoreceptor was produced by exactly the same method.

Working Example 45

Aside from using ethylene compound No. I-45 (wherein $R_1$, $R_2$ and $R_3$ are at para positions) instead of the ethylene compound (No. I-1) used in Working Example 1, an electrophotographic photoreceptor was produced by exactly the same method.

Working Example 46

Aside from using ethylene compound No. I-46 instead of the ethylene compound (No. I-1) used in Working Example 1, an electrophotographic photoreceptor was produced by exactly the same method.

Working Example 47

Aside from using ethylene compound No. I-47 (wherein $R_1$ and $R_2$ are at para positions) instead of the ethylene compound (No. I-1) used in Working Example 1, an electrophotographic photoreceptor was produced by exactly the same method.

Working Example 48

Aside from using ethylene compound No. I-48 (wherein $R_1$, $R_2$ and $R_3$ are at para positions) instead of the ethylene compound (No. I-1) used in Working Example 1, an electrophotographic photoreceptor was produced by exactly the same method.

Working Example 49

Aside from using ethylene compound No. I-49 instead of the ethylene compound (No. I-1) used in Working Example 1, an electrophotographic photoreceptor was produced by exactly the same method.

Working Example 50

Aside from using ethylene compound No. I-50 (wherein $R_1$ and $R_2$ are at para positions) instead of the ethylene compound (No. I-1) used in Working Example 1, an electrophotographic photoreceptor was produced by exactly the same method.

Working Example 51

Aside from using ethylene compound No. I-51 (wherein $R_1$, $R_2$ and $R_3$ are at para positions) instead of the ethylene compound (No. I-1) used in Working Example 1, an electrophotographic photoreceptor was produced by exactly the same method.

Working Example 52

Aside from using ethylene compound No. I-52 instead of the ethylene compound (No. I-1) used in Working Example 1, an electrophotographic photoreceptor was produced by exactly the same method.

Working Example 53

Aside from using ethylene compound No. I-53 (wherein $R_1$ and $R_2$ are at para positions) instead of the ethylene compound (No. I-1) used in Working Example 1, an electrophotographic photoreceptor was produced by exactly the same method.

Working Example 54

Aside from using ethylene compound No. I-54 (wherein $R_1$, $R_2$ and $R_3$ are at para positions) instead of the ethylene compound (No. I-1) used in Working Example 1, an electrophotographic photoreceptor was produced by exactly the same method.

Working Example 55

Aside from using ethylene compound No. I-55 instead of the ethylene compound (No. I-1) used in Working Example 1, an electrophotographic photoreceptor was produced by exactly the same method.

Working Example 56

Aside from using ethylene compound No. I-56 (wherein $R_1$ and $R_2$ are at para positions) instead of the ethylene compound (No. I-1) used in Working Example 1, an electrophotographic photoreceptor was produced by exactly the same method.

Working Example 57

Aside from using ethylene compound No. I-57 (wherein $R_1$, $R_2$ and $R_3$ are at para positions) instead of the ethylene compound (No. I-1) used in Working Example 1, an electrophotographic photoreceptor was produced by exactly the same method.

Working Example 58

Aside from using ethylene compound No. I-58 instead of the ethylene compound (No. I-1) used in Working Example 1, an electrophotographic photoreceptor was produced by exactly the same method.

Working Example 59

Aside from using ethylene compound No. I-59 (wherein $R_1$ and $R_2$ are at para positions) instead of the ethylene compound (No. I-1) used in Working Example 1, an electrophotographic photoreceptor was produced by exactly the same method.

Working Example 60

Aside from using ethylene compound No. I-60 (wherein $R_1$, $R_2$ and $R_3$ are at para positions) instead of the ethylene compound (No. I-1) used in Working Example 1, an electrophotographic photoreceptor was produced by exactly the same method.

Working Example 61

Aside from using ethylene compound No. I-61 instead of the ethylene compound (No. I-1) used in Working Example 1, an electrophotographic photoreceptor was produced by exactly the same method.

Working Example 62

Aside from using ethylene compound No. I-62 (wherein $R_1$ and $R_2$ are at para positions) instead of the ethylene compound (No. I-1) used in Working Example 1, an electrophotographic photoreceptor was produced by exactly the same method.

Working Example 63

Aside from using ethylene compound No. I-63 (wherein $R_1$, $R_2$ and $R_3$ are at para positions) instead of the ethylene compound (No. I-1) used in Working Example 1, an electrophotographic photoreceptor was produced by exactly the same method.

Working Example 64

Aside from using ethylene compound No. I-64 instead of the ethylene compound (No. I-1) used in Working Example 1, an electrophotographic photoreceptor was produced by exactly the same method.

Working Example 65

Aside from using ethylene compound No. I-65 (wherein $R_1$ and $R_2$ are at para positions) instead of the ethylene compound (No. I-1) used in Working Example 1, an electrophotographic photoreceptor was produced by exactly the same method.

Working Example 66

Aside from using ethylene compound No. I-66 (wherein $R_1$, $R_2$ and $R_3$ are at para positions) instead of the ethylene compound (No. I-1) used in Working Example 1, an electrophotographic photoreceptor was produced by exactly the same method.

Working Example 67

Aside from using ethylene compound No. I-67 instead of the ethylene compound (No. I-1) used in Working Example 1, an electrophotographic photoreceptor was produced by exactly the same method.

Working Example 68

Aside from using ethylene compound No. I-68 (wherein $R_1$ and $R_2$ are at para positions) instead of the ethylene compound (No. I-1) used in Working Example 1, an electrophotographic photoreceptor was produced by exactly the same method.

Working Example 69

Aside from using ethylene compound No. I-69 (wherein $R_1$, $R_2$ and $R_3$ are at para positions) instead of the ethylene compound (No. I-1) used in Working Example 1, an electrophotographic photoreceptor was produced by exactly the same method.

Working Example 70

Aside from using ethylene compound No. I-70 instead of the ethylene compound (No. I-1) used in Working Example 1, an electrophotographic photoreceptor was produced by exactly the same method.

Working Example 71

Aside from using ethylene compound No. I-71 (wherein $R_1$ and $R_2$ are at para positions) instead of the ethylene compound (No. I-1) used in Working Example 1, an electrophotographic photoreceptor was produced by exactly the same method.

Working Example 72

Aside from using ethylene compound No. I-72 (wherein $R_1$, $R_2$ and $R_3$ are at para positions) instead of the ethylene compound (No. I-1) used in Working Example 1, an electrophotographic photoreceptor was produced by exactly the same method.

Working Example 73

Aside from using ethylene compound No. I-73 instead of the ethylene compound (No. I-1) used in Working Example 1, an electrophotographic photoreceptor was produced by exactly the same method.

Working Example 74

Aside from using ethylene compound No. I-74 (wherein $R_1$ and $R_2$ are at para positions) instead of the ethylene compound (No. I-1) used in Working Example 1, an electrophotographic photoreceptor was produced by exactly the same method.

Working Example 75

Aside from using ethylene compound No. I-75 (wherein $R_1$, $R_2$ and $R_3$ are at para positions) instead of the ethylene compound (No. I-1) used in Working Example 1, an electrophotographic photoreceptor was produced by exactly the same method.

Working Example 76

Aside from using ethylene compound No. I-76 instead of the ethylene compound (No. I-1) used in Working Example 1, an electrophotographic photoreceptor was produced by exactly the same method.

Working Example 77

Aside from using ethylene compound No. I-77 (wherein $R_1$ and $R_2$ are at para positions) instead of the ethylene compound (No. I-1) used in Working Example 1, an electrophotographic photoreceptor was produced by exactly the same method.

Working Example 78

Aside from using ethylene compound No. I-78 (wherein $R_1$, $R_2$ and $R_3$ are at para positions) instead of the ethylene compound (No. I-1) used in Working Example 1, an electrophotographic photoreceptor was produced by exactly the same method.

Working Example 79

Aside from using ethylene compound No. I-79 instead of the ethylene compound (No. I-1) used in Working Example 1, an electrophotographic photoreceptor was produced by exactly the same method.

Working Example 80

Aside from using ethylene compound No. I-80 (wherein $R_1$ and $R_2$ are at para positions) instead of the ethylene compound (No. I-1) used in Working Example 1, an electrophotographic photoreceptor was produced by exactly the same method.

Working Example 81

Aside from using ethylene compound No. I-81 (wherein $R_1$, $R_2$ and $R_3$ are at para positions) instead of the ethylene compound (No. I-1) used in Working Example 1, an electrophotographic photoreceptor was produced by exactly the same method.

Working Example 82

Aside from using ethylene compound No. I-82 instead of the ethylene compound (No. I-1) used in Working Example 1, an electrophotographic photoreceptor was produced by exactly the same method.

Working Example 83

Aside from using ethylene compound No. I-83 (wherein $R_1$ and $R_2$ are at para positions) instead of the ethylene compound (No. I-1) used in Working Example 1, an electrophotographic photoreceptor was produced by exactly the same method.

Working Example 84

Aside from using ethylene compound No. I-84 (wherein $R_1$, $R_2$ and $R_3$ are at para positions) instead of the ethylene compound (No. I-1) used in Working Example 1, an electrophotographic photoreceptor was produced by exactly the same method.

Working Example 85

Aside from using ethylene compound No. I-85 instead of the ethylene compound (No. I-1) used in Working Example 1, an electrophotographic photoreceptor was produced by exactly the same method.

Working Example 86

Aside from using ethylene compound No. I-86 (wherein $R_1$ and $R_2$ are at para positions) instead of the ethylene compound (No. I-1) used in Working Example 1, an electrophotographic photoreceptor was produced by exactly the same method.

Working Example 87

Aside from using ethylene compound No. I-87 (wherein $R_1$, $R_2$ and $R_3$ are at para positions) instead of the ethylene compound (No. I-1) used in Working Example 1, an electrophotographic photoreceptor was produced by exactly the same method.

Working Example 88

Aside from using ethylene compound No. I-88 instead of the ethylene compound (No. I-1) used in Working Example 1, an electrophotographic photoreceptor was produced by exactly the same method.

Working Example 89

Aside from using ethylene compound No. I-89 (wherein $R_1$ and $R_2$ are at para positions) instead of the ethylene compound (No. I-1) used in Working Example 1, an electrophotographic photoreceptor was produced by exactly the same method.

Working Example 90

Aside from using ethylene compound No. I-90 (wherein $R_1$, $R_2$ and $R_3$ are at para positions) instead of the ethylene compound (No. I-1) used in Working Example 1, an electrophotographic photoreceptor was produced by exactly the same method.

Working Example 91

Aside from using ethylene compound No. I-91 instead of the ethylene compound (No. I-1) used in Working Example 1, an electrophotographic photoreceptor was produced by exactly the same method.

Working Example 92

Aside from using ethylene compound No. I-92 (wherein $R_1$ and $R_2$ are at para positions) instead of the ethylene compound (No. I-1) used in Working Example 1, an electrophotographic photoreceptor was produced by exactly the same method.

Working Example 93

Aside from using ethylene compound No. I-93 (wherein $R_1$, $R_2$ and $R_3$ are at para positions) instead of the ethylene compound (No. I-1) used in Working Example 1, an electrophotographic photoreceptor was produced by exactly the same method.

Working Example 94

Aside from using ethylene compound No. I-94 instead of the ethylene compound (No. I-1) used in Working Example 1, an electrophotographic photoreceptor was produced by exactly the same method.

Working Example 95

Aside from using ethylene compound No. I-95 (wherein $R_1$ and $R_2$ are at para positions) instead of the ethylene compound (No. I-1) used in Working Example 1, an electrophotographic photoreceptor was produced by exactly the same method.

Working Example 96

Aside from using ethylene compound No. I-96 (wherein $R_1$, $R_2$ and $R_3$ are at para positions) instead of the ethylene compound (No. I-1) used in Working Example 1, an electrophotographic photoreceptor was produced by exactly the same method.

Working Example 97

Aside from using ethylene compound No. I-97 instead of the ethylene compound (No. I-1) used in Working Example 1, an electrophotographic photoreceptor was produced by exactly the same method.

Working Example 98

Aside from using ethylene compound No. I-98 (wherein $R_1$ and $R_2$ are at para positions) instead of the ethylene compound (No. I-1) used in Working Example 1, an electrophotographic photoreceptor was produced by exactly the same method.

Working Example 99

Aside from using ethylene compound No. I-99 (wherein $R_1$, $R_2$ and $R_3$ are at para positions) instead of the ethylene compound (No. I-1) used in Working Example 1, an electrophotographic photoreceptor was produced by exactly the same method.

Working Example 100

Aside from using ethylene compound No. I-100 instead of the ethylene compound (No. I-1) used in Working Example 1, an electrophotographic photoreceptor was produced by exactly the same method.

Working Example 101

Aside from using ethylene compound No. I-101 (wherein $R_1$ and $R_2$ are at para positions) instead of the ethylene compound (No. I-1) used in Working Example 1, an electrophotographic photoreceptor was produced by exactly the same method.

Working Example 102

Aside from using ethylene compound No. I-102 (wherein $R_1$, $R_2$ and $R_3$ are at para positions) instead of the ethylene compound (No. I-1) used in Working Example 1, an electrophotographic photoreceptor was produced by exactly the same method.

Working Example 103

Aside from using ethylene compound No. I-103 instead of the ethylene compound (No. I-1) used in Working Example 1, an electrophotographic photoreceptor was produced by exactly the same method.

Working Example 104

Aside from using ethylene compound No. I-104 (wherein $R_1$ and $R_2$ are at para positions) instead of the ethylene compound (No. I-1) used in Working Example 1, an electrophotographic photoreceptor was produced by exactly the same method.

Working Example 105

Aside from using ethylene compound No. I-105 (wherein $R_1$, $R_2$ and $R_3$ are at para positions) instead of the ethylene compound (No. I-1) used in Working Example 1, an electrophotographic photoreceptor was produced by exactly the same method.

Working Example 106

Aside from using ethylene compound No. I-106 instead of the ethylene compound (No. I-1) used in Working Example 1, an electrophotographic photoreceptor was produced by exactly the same method.

Working Example 107

Aside from using ethylene compound No. I-107 (wherein $R_1$ and $R_2$ are at para positions) instead of the ethylene compound (No. I-1) used in Working Example 1, an electrophotographic photoreceptor was produced by exactly the same method.

Working Example 108

Aside from using ethylene compound No. I-108 (wherein $R_1$, $R_2$ and $R_3$ are at para positions) instead of the ethylene compound (No. I-1) used in Working Example 1, an electrophotographic photoreceptor was produced by exactly the same method.

Working Example 109

Aside from using Y-type titanyl phthalocyanine instead of the charge generation material used in Working Example 1, an electrophotographic photoreceptor was produced by the same method as in Working Example 1.

Working Example 110

Aside from using metal-free phthalocyanine instead of the charge generation material used in Working Example 1, an electrophotographic photoreceptor was produced by the same method as in Working Example 1.

Working Example 111

Aside from using a polycarbonate resin (PCZ-500, available from Mitsubishi Gas Chemical Company, Inc.) instead of the resin binder in the charge transport layer used in Working Example 1, an electrophotographic photoreceptor was produced by the same method as in Working Example 1.

Working Example 112

Aside from using a polycarbonate resin (S3000, available from Mitsubishi Engineering Plastics-Corporation) instead of the resin binder in the charge transport layer used in Working Example 1, an electrophotographic photoreceptor was produced by the same method as in Working Example 1.

Comparative Example 1

Aside from using the known charge transport material compound (No. I-109) shown in Table 5 below instead of the ethylene compound (No. I-1) used in Working Example 1, an electrophotographic photoreceptor was produced by exactly the same method. The symbols in Table 5 have the same meanings as in Tables 1 to 4 above.

Comparative Example 2

Aside from using the known charge transport compound (No. I-110) shown in Table 5 below instead of the ethylene compound (No. I-1) used in Working Example 1, an electrophotographic photoreceptor was produced by exactly the same method.

Comparative Example 3

Aside from using the known charge transport compound (No. I-111) shown in Table 5 below instead of the ethylene compound (No. I-1) used in Working Example 1, an electrophotographic photoreceptor was produced by exactly the same method.

TABLE 5

| Compound No. | Group in general formula (I) | | | | |
|---|---|---|---|---|---|
| | $R_1$ | $R_2$ | $R_3$ | $R_4$ | Ar |
| I-109 | H | H | H | H | *1 |
| I-110 | H | H | H | H | *7 |
| I-111 | H | H | H | H | *9 |

Production of Single Layer Type Photoreceptors:

Working Example 113

A liquid coating prepared by stirring and dissolving 0.2 part by weight of a vinyl chloride-vinyl acetate-vinyl alcohol copolymer (available from Nisshin Chemical Industry Co., Ltd. under the trade name Solbine TA5R) in 99 parts by weight of methyl ethyl ketone was dip-coated as the undercoat layer onto the outer periphery of an aluminum cylinder having an outside diameter of 24 mm as the conductive substrate 1 and dried at a temperature of 100° C. for 30 minutes, thereby forming an undercoat layer 20 having a film thickness of 0.1 μm.

A liquid coating prepared by dissolving and dispersing 1 part by weight of metal-free phthalocyanine of the following formula

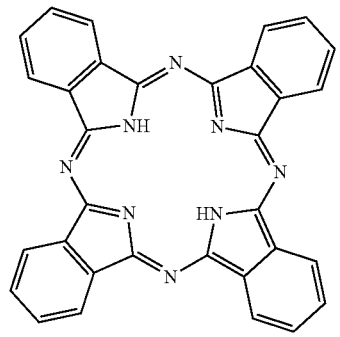 [SMILES: c1ccc2c(c1)-c1nc-2nc2[nH]c(nc3nc(nc4[nH]c(n1)c1ccccc41)-c1ccccc1-3)c1ccccc21]

as the charge generation material, 45 parts by weight of Compound (I-1) as the hole transporting agent, 30 parts by weight of the compound of the following formula

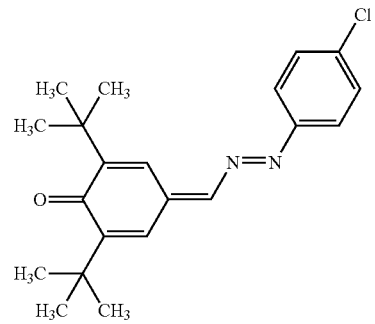 [SMILES: CC(C)(C)C1=CC(=C/N=N/c2ccc(Cl)cc2)C=C(C(C)(C)C)C1=O]

as the electron transporting agent and 55 parts by weight of a polycarbonate resin (PCZ-500 (trade name), available from Mitsubishi Gas Chemical Company, Inc.) as the resin binder in 350 parts by weight of tetrahydrofuran was dip-coated onto this undercoat layer 20 and dried at a temperature of 100° C. for 60 minutes, thereby forming a photosensitive layer having a film thickness of 25 μM and completing production of a single layer type photoreceptor.

Working Example 114

Aside from replacing Compound (I-1) used in Working Example 113 with Compound (I-37), a single layer type photoreceptor was produced by the same method as in Working Example 113.

Working Example 115

Aside from replacing the metal-free phthalocyanine used in Working Example 113 with Y-type titanyl phthalocyanine, a single layer type photoreceptor was produced by the same method as in Working Example 113.

Comparative Example 4

Aside from replacing Compound (I-1) used in Working Example 113 with Compound (I-109) of Comparative Example 1, a single layer type photoreceptor was produced by the same method as in Working Example 113.

Production of Positive-Charging Multi Layer Photoreceptors:

Working Example 116

A liquid coating was prepared by dissolving 50 parts by weight of Compound I-1 as the charge transport material and 50 parts by weight of a polycarbonate resin (PCZ-500 (trade name), available from Mitsubishi Gas Chemical Company, Inc.) as the resin binder in 800 parts by weight of dichloromethane. An aluminum cylinder having an outside diameter of 24 mm was used as the conductive substrate 1. The liquid coating was dip-coated onto the outer periphery of the aluminum cylinder and dried at a temperature of 120° C. for 60 minutes, thereby forming a charge transport layer having a film thickness of 15 μm.

A liquid coating prepared by dissolving and dispersing 1.5 parts by weight of metal-free phthalocyanine of the following formula

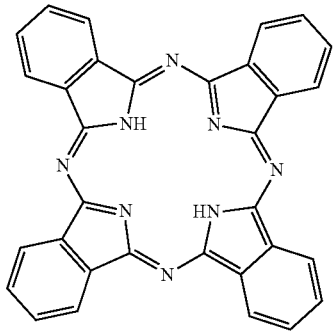 [SMILES: c1ccc2c(c1)-c1nc-2nc2[nH]c(nc3nc(nc4[nH]c(n1)c1ccccc41)-c1ccccc1-3)c1ccccc21]

as the charge generation material, 10 parts by weight of Compound (I-1) as the hole transporting agent, 25 parts by weight of the compound of the following formula

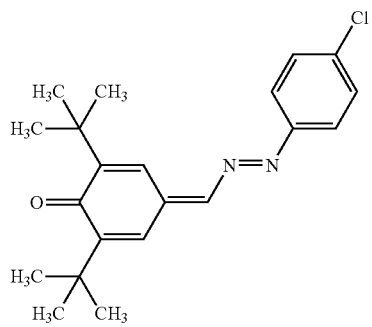 [SMILES: CC(C)(C)C1=CC(=C/N=N/c2ccc(Cl)cc2)C=C(C(C)(C)C)C1=O]

as an electron transporting agent and 60 parts by weight of a polycarbonate resin (PCZ-500 (trade name), available from Mitsubishi Gas Chemical Company, Inc.) as the resin binder in 800 parts by weight of 1,2-dichloroethane was dip-coated onto this charge transport layer. The liquid coating was then dried at a temperature of 100° C. for 60 minutes, thereby forming a photosensitive layer having a film thickness of 15 μm and completing production of a positive-charging multi layer photoreceptor.

Working Example 117

Aside from replacing the metal-free phthalocyanine used in Working Example 116 with Y-type titanyl phthalocyanine, a positive-charging multi layer photoreceptor was produced by the same method as in Working Example 116.

Comparative Example 5

Aside from replacing Compound (I-1) used in Working Example 116 with Compound (I-109), a positive-charging multi layer photoreceptor was produced by the same method as in Working Example 116.

Evaluation:

The electrophotographic photoreceptors obtained in Working Examples 1 to 112 and Comparative Examples 1 to 3 were loaded into commercial printers (LJ-4000, manufactured by Hewlett-Packard Development Company) that had been modified so as to enable measurement of the potential at the surface of the photoreceptor, and the bright area potential (bright area potential before printing and light exposure) within the printer was measured. In addition, the photoreceptors were exposed to light by being left for 12 hours under a 1500 lx·s fluorescent light, following which they were similarly loaded into LJ-4000 printers and the bright area potential (bright area potential after light exposure) was measured. The results are shown in Tables 6 to 12 below. Moreover, drums produced in the same way were loaded into the printers and 10,000 sheets of A4 paper were printed, following which the bright area potential (bright area potential after printing 10,000 sheets) was measured. The results indicate that, as the amount of change in the potential before and after light exposure and the amount of change in the potential before and after printing 10,000 sheets, i.e., the absolute values of the before-and-after differences therebetween, becomes smaller, the fluctuations in potential become lower, photodeterioration decreases and light-induced fatigue diminishes.

The electrophotographic photoreceptors produced in Working Examples 113 to 116 and Comparative Examples 4 and 5 were loaded into HL-2040 printers manufactured by Brother Industries, Ltd. that had been modified so as to enable measurement of the potential at the surface of the photoreceptor, and the potential at exposed areas of the surface was measured. The bright area potential within the printers (potential of bright areas before printing and light exposure) was measured. In addition, the photoreceptors were exposed to light by being left for 12 hours under a 1500 lx·s fluorescent light, following which they were similarly loaded into HL-2040 printers and the bright area potential (bright area potential after light exposure) was measured. The results are shown in Table 13 below. Moreover, drums produced in the same way were loaded into the printers and 10,000 sheets of A4 paper were printed, following which the bright area potential (bright area potential after printing 10,000 sheets) was measured. The results indicate that, as the amount of change in the potential before and after light exposure and the amount of change in the potential before and after printing 10,000 sheets, i.e., the absolute values of the before-and-after differences therebetween, becomes smaller, the fluctuations in potential become lower, photodeterioration decreases and light-induced fatigue diminishes.

TABLE 6

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 1 | I-1 | 92 | 104 | −12 | 97 | −5 |
| Working Example 2 | I-2 | 101 | 105 | −4 | 108 | −7 |
| Working Example 3 | I-3 | 111 | 121 | −10 | 121 | −10 |
| Working Example 4 | I-4 | 93 | 101 | −8 | 102 | −9 |
| Working Example 5 | I-5 | 108 | 116 | −8 | 116 | −8 |
| Working Example 6 | I-6 | 112 | 122 | −10 | 118 | −6 |
| Working Example 7 | I-7 | 108 | 115 | −7 | 117 | −9 |
| Working Example 8 | I-8 | 96 | 112 | −16 | 105 | −9 |
| Working Example 9 | I-9 | 113 | 120 | −7 | 123 | −10 |
| Working Example 10 | I-10 | 102 | 108 | −6 | 110 | −8 |
| Working Example 11 | I-11 | 98 | 103 | −5 | 104 | −6 |
| Working Example 12 | I-12 | 110 | 118 | −8 | 119 | −9 |
| Working Example 13 | I-13 | 116 | 123 | −7 | 122 | −6 |
| Working Example 14 | I-14 | 105 | 117 | −12 | 114 | −9 |
| Working Example 15 | I-15 | 99 | 109 | −10 | 104 | −5 |
| Working Example 16 | I-16 | 95 | 106 | −11 | 100 | −5 |
| Working Example 17 | I-17 | 104 | 111 | −7 | 113 | −9 |
| Working Example 18 | I-18 | 107 | 119 | −12 | 115 | −8 |

TABLE 7

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 19 | I-19 | 94 | 111 | −17 | 102 | −8 |
| Working Example 20 | I-20 | 98 | 106 | −8 | 108 | −10 |
| Working Example 21 | I-21 | 115 | 120 | −5 | 120 | −5 |
| Working Example 22 | I-22 | 96 | 102 | −6 | 102 | −6 |
| Working Example 23 | I-23 | 104 | 113 | −9 | 113 | −9 |
| Working Example 24 | I-24 | 115 | 121 | −6 | 122 | −7 |
| Working Example 25 | I-25 | 103 | 110 | −7 | 109 | −6 |

TABLE 7-continued

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 26 | I-26 | 99 | 111 | −12 | 108 | −9 |
| Working Example 27 | I-27 | 110 | 118 | −8 | 119 | −9 |
| Working Example 28 | I-28 | 101 | 106 | −5 | 107 | −6 |
| Working Example 29 | I-29 | 103 | 112 | −9 | 110 | −7 |
| Working Example 30 | I-30 | 105 | 113 | −8 | 112 | −7 |
| Working Example 31 | I-31 | 113 | 121 | −8 | 119 | −6 |
| Working Example 32 | I-32 | 102 | 116 | −14 | 109 | −7 |
| Working Example 33 | I-33 | 101 | 113 | −12 | 110 | −9 |
| Working Example 34 | I-34 | 100 | 109 | −9 | 109 | −9 |
| Working Example 35 | I-35 | 102 | 115 | −13 | 109 | −7 |
| Working Example 36 | I-36 | 103 | 117 | −14 | 109 | −6 |

TABLE 8

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 37 | I-37 | 100 | 112 | −12 | 109 | −9 |
| Working Example 38 | I-38 | 95 | 103 | −8 | 101 | −6 |
| Working Example 39 | I-39 | 112 | 121 | −9 | 121 | −9 |
| Working Example 40 | I-40 | 101 | 115 | −14 | 107 | −6 |
| Working Example 41 | I-41 | 96 | 110 | −14 | 101 | −5 |
| Working Example 42 | I-42 | 112 | 121 | −9 | 119 | −7 |
| Working Example 43 | I-43 | 107 | 120 | −13 | 116 | −9 |
| Working Example 44 | I-44 | 94 | 111 | −17 | 99 | −5 |
| Working Example 45 | I-45 | 111 | 121 | −10 | 120 | −9 |
| Working Example 46 | I-46 | 102 | 108 | −6 | 108 | −6 |
| Working Example 47 | I-47 | 99 | 113 | −14 | 104 | −5 |
| Working Example 48 | I-48 | 98 | 110 | −12 | 103 | −5 |
| Working Example 49 | I-49 | 108 | 119 | −11 | 114 | −6 |
| Working Example 50 | I-50 | 105 | 118 | −13 | 115 | −10 |

TABLE 8-continued

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 51 | I-51 | 97 | 116 | −19 | 105 | −8 |
| Working Example 52 | I-52 | 98 | 106 | −8 | 107 | −9 |
| Working Example 53 | I-53 | 97 | 113 | −16 | 107 | −10 |
| Working Example 54 | I-54 | 101 | 111 | −10 | 107 | −6 |

TABLE 9

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 55 | I-55 | 99 | 106 | −7 | 105 | −6 |
| Working Example 56 | I-56 | 104 | 113 | −9 | 114 | −10 |
| Working Example 57 | I-57 | 110 | 121 | −11 | 115 | −5 |
| Working Example 58 | I-58 | 93 | 103 | −10 | 101 | −8 |
| Working Example 59 | I-59 | 102 | 114 | −12 | 109 | −7 |
| Working Example 60 | I-60 | 103 | 118 | −15 | 108 | −5 |
| Working Example 61 | I-61 | 96 | 108 | −12 | 104 | −8 |
| Working Example 62 | I-62 | 101 | 115 | −14 | 109 | −8 |
| Working Example 63 | I-63 | 99 | 106 | −7 | 108 | −9 |
| Working Example 64 | I-64 | 98 | 108 | −10 | 105 | −7 |
| Working Example 65 | I-65 | 111 | 119 | −8 | 116 | −5 |
| Working Example 66 | I-66 | 102 | 113 | −11 | 112 | −10 |
| Working Example 67 | I-67 | 114 | 122 | −8 | 124 | −10 |
| Working Example 68 | I-68 | 99 | 113 | −14 | 105 | −6 |
| Working Example 69 | I-69 | 102 | 110 | −8 | 111 | −9 |
| Working Example 70 | I-70 | 102 | 111 | −9 | 109 | −7 |
| Working Example 71 | I-71 | 103 | 113 | −10 | 110 | −7 |
| Working Example 72 | I-72 | 98 | 112 | −14 | 105 | −7 |

TABLE 10

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 73 | I-73 | 99 | 105 | −6 | 107 | −8 |
| Working Example 74 | I-74 | 95 | 104 | −9 | 103 | −8 |
| Working Example 75 | I-75 | 109 | 121 | −12 | 114 | −5 |
| Working Example 76 | I-76 | 95 | 103 | −8 | 102 | −7 |
| Working Example 77 | I-77 | 100 | 112 | −12 | 106 | −6 |
| Working Example 78 | I-78 | 109 | 120 | −11 | 118 | −9 |
| Working Example 79 | I-79 | 102 | 113 | −11 | 108 | −6 |
| Working Example 80 | I-80 | 101 | 112 | −11 | 111 | −10 |
| Working Example 81 | I-81 | 96 | 112 | −16 | 103 | −7 |
| Working Example 82 | I-82 | 104 | 117 | −13 | 110 | −6 |
| Working Example 83 | I-83 | 98 | 112 | −14 | 104 | −6 |
| Working Example 84 | I-84 | 103 | 115 | −12 | 111 | −8 |
| Working Example 85 | I-85 | 106 | 112 | −6 | 111 | −5 |
| Working Example 86 | I-86 | 99 | 114 | −15 | 107 | −8 |
| Working Example 87 | I-87 | 102 | 117 | −15 | 110 | −8 |
| Working Example 88 | I-88 | 98 | 106 | −8 | 104 | −6 |
| Working Example 89 | I-89 | 101 | 114 | −13 | 107 | −6 |
| Working Example 90 | I-90 | 104 | 118 | −14 | 113 | −9 |

TABLE 11

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 91 | I-91 | 101 | 113 | −12 | 108 | −7 |
| Working Example 92 | I-92 | 103 | 109 | −6 | 109 | −6 |
| Working Example 93 | I-93 | 112 | 120 | −8 | 118 | −6 |
| Working Example 94 | I-94 | 97 | 104 | −7 | 104 | −7 |
| Working Example 95 | I-95 | 99 | 112 | −13 | 107 | −8 |
| Working Example 96 | I-96 | 102 | 119 | −17 | 108 | −6 |
| Working Example 97 | I-97 | 104 | 121 | −17 | 113 | −9 |

TABLE 11-continued

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 98 | I-98 | 103 | 113 | −10 | 110 | −7 |
| Working Example 99 | I-99 | 97 | 115 | −18 | 107 | −10 |
| Working Example 100 | I-100 | 95 | 103 | −8 | 101 | −6 |
| Working Example 101 | I-101 | 102 | 114 | −12 | 111 | −9 |
| Working Example 102 | I-102 | 99 | 112 | −13 | 105 | −6 |
| Working Example 103 | I-103 | 98 | 115 | −17 | 106 | −8 |
| Working Example 104 | I-104 | 102 | 112 | −10 | 111 | −9 |
| Working Example 105 | I-105 | 105 | 113 | −8 | 114 | −9 |
| Working Example 106 | I-106 | 97 | 108 | −11 | 105 | −8 |
| Working Example 107 | I-107 | 99 | 113 | −14 | 107 | −8 |
| Working Example 108 | I-108 | 102 | 114 | −12 | 112 | −10 |

TABLE 12

| | Compound No. | Bright area potential ($V_L$) before printing and exposure to light (−V) | Bright area potential ($V_L$) after exposure to light (−V) | Change in potential (ΔVL) before and after exposure to light (−V) | Bright area potential ($V_L$) after printing 10,000 sheets (−V) | Change in potential (ΔVL) before and after printing 10,000 sheets (−V) |
|---|---|---|---|---|---|---|
| Working Example 109 | I-1 | 85 | 88 | −3 | 92 | −7 |
| Working Example 110 | I-1 | 125 | 127 | −2 | 133 | −8 |
| Working Example 111 | I-1 | 99 | 112 | −13 | 106 | −7 |
| Working Example 112 | I-1 | 105 | 112 | −7 | 112 | −7 |
| Comparative Example 1 | I-109 | 97 | 245 | −148 | 205 | −108 |
| Comparative Example 2 | I-110 | 103 | 263 | −160 | 229 | −126 |
| Comparative Example 3 | I-111 | 106 | 212 | −106 | 241 | −135 |

TABLE 13

| | Compound No. | Bright area potential ($V_L$) before printing and exposure to light (V) | Bright area potential ($V_L$) after exposure to light (V) | Change in potential ($\Delta VL$) before and after exposure to light (V) | Bright area potential ($V_L$) after printing 10,000 sheets (V) | Change in potential ($\Delta VL$) before and after printing 10,000 sheets (V) |
|---|---|---|---|---|---|---|
| Working Example 113 | I-1 | 123 | 126 | 3 | 130 | 7 |
| Working Example 114 | I-37 | 122 | 129 | 7 | 131 | 9 |
| Working Example 115 | I-1 | 105 | 110 | 5 | 114 | 9 |
| Comparative Example 4 | I-109 | 127 | 163 | 36 | 178 | 51 |
| Comparative Example 5 | I-109 | 126 | 159 | 33 | 174 | 48 |
| Working Example 116 | I-1 | 118 | 122 | 4 | 123 | 5 |
| Working Example 117 | I-1 | 105 | 108 | 3 | 112 | 7 |
| Comparative Example 6 | I-109 | 121 | 150 | 29 | 169 | 48 |

The photoreceptors of the present invention, in the evaluations before and after printing 10,000 sheets in a printer, were able to prevent an increase in residual potential. Also, because the fluctuation in the bright area potential before and after exposure to light is small, it is apparent that when the inventive photoreceptors are used for an extended period of time, they will have stable properties as electrophotographic photoreceptors and possess excellent light-induced fatigue characteristics.

The invention claimed is:

1. A charge transport material having reduced photodeterioration, comprising an ethylene compound having an ethylene double bond site, having a structure in which four different substituents are substituted at the ethylene double bond site, and having general formula (I) below

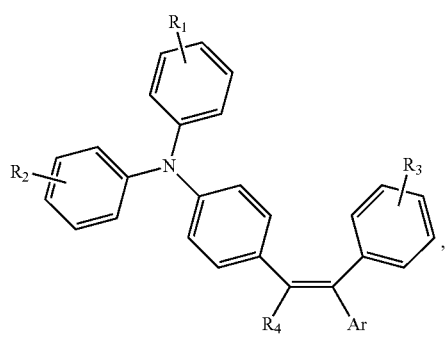

where $R_1$, $R_2$ and $R_3$ are each independently a hydrogen atom, a halogen atom, an alkyl group of 1 to 6 carbons or an alkoxyl group of 1 to 6 carbons; $R_4$ is phenyl or tolyl; and Ar is one group selected from the group consisting of naphthyl, biphenyl, anthryl, xylyl, and phenanthryl.

2. An electrophotographic photoreceptor, comprising:
a conductive substrate; and
a photosensitive layer provided on the conductive substrate and comprising a charge transport material that is an ethylene compound having an ethylene double bond site, having a structure in which four different substituents are substituted at the ethylene double bond site, and having general formula (I) below

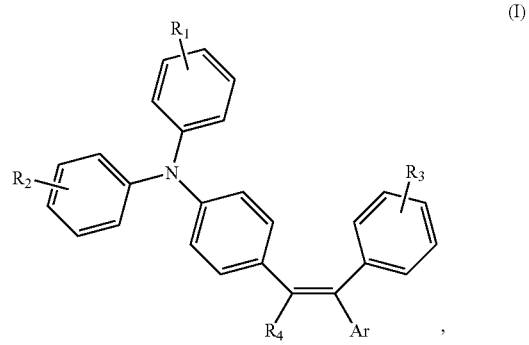

where $R_1$, $R_2$ and $R_3$ are each independently a hydrogen atom, a halogen atom, an alkyl group of 1 to 6 carbons or an alkoxyl group of 1 to 6 carbons; $R_4$ is phenyl or tolyl; and Ar is one group selected from the group consisting of naphthyl, biphenyl, anthryl, xylyl, and phenanthryl.

3. The electrophotographic photoreceptor according to claim 2, wherein the ethylene compound is at least one ethylene compound having a structure selected from the group consisting of E-forms and Z-forms thereof.

4. The electrophotographic photoreceptor according to claim 2, wherein $R_4$ in general formula (I) is one group selected from the group consisting of methyl, ethyl, propyl, isopropyl, phenyl and tolyl.

5. The electrophotographic photoreceptor according to claim 2, wherein, in general formula (I), at least two of $R_1$, $R_2$ and $R_3$ are hydrogen atoms or methyl groups.

6. The electrophotographic photoreceptor according to claim 2, wherein, in general formula (I), $R_1$, $R_2$ and $R_3$ are hydrogen atoms.

7. The electrophotographic photoreceptor according to claim 6, wherein, in general formula (I), $R_4$ is a methyl group.

8. The electrophotographic photoreceptor according to claim 7, wherein, in general formula (I), Ar is anthryl.

9. The electrophotographic photoreceptor according to claim 2, wherein the photosensitive layer further comprises a charge generation material.

10. The electrophotographic photoreceptor according to claim 9, wherein the charge generation material is at least one material selected from the group consisting of titanyl phthalocyanine and metal-free phthalocyanine.

11. The electrophotographic photoreceptor according to claim 9, wherein the photosensitive layer is a laminate of a charge generation layer containing the charge generation material and a charge transport layer containing the charge transport material that is obtained by successive lamination.

12. The electrophotographic photoreceptor according to claim 9, wherein the photosensitive layer comprises a single layer containing both the charge generation material and the charge transport material.

13. A process for producing an electrophotographic photoreceptor, comprising the steps of:

providing a charge transport material that is an ethylene compound having an ethylene double bond site, having a structure in which four different substituents are substituted at the ethylene double bond site, and having general formula (I) below

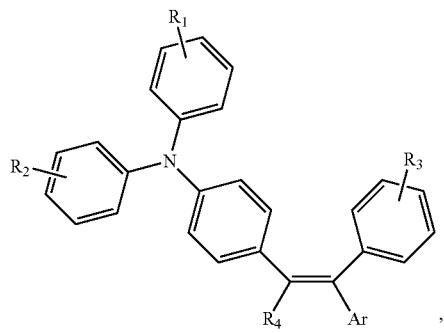

where $R_1$, $R_2$ and $R_3$ are each independently a hydrogen atom, a halogen atom, an alkyl group of 1 to 6 carbons or an alkoxyl group of 1 to 6 carbons; $R_4$ is phenyl or tolyl; and Ar is one group selected from the group consisting of naphthyl, biphenyl, anthryl, xylyl, and phenanthryl; and forming a photosensitive layer by applying, onto a conductive substrate, a liquid coating material containing the ethylene compound.

14. The process according to claim 13, wherein the liquid coating material further comprises a charge generation material and a resin binder.

* * * * *